(12) United States Patent
Shiku et al.

(10) Patent No.: US 11,083,744 B2
(45) Date of Patent: Aug. 10, 2021

(54) THERAPEUTIC AGENT ASSOCIATED WITH SUPPRESSION OF PROLIFERATION AND METASTASIS OF TUMOR, WHICH COMPRISES EXOSOMES RELEASED FROM CYTOTOXIC T CELLS AND TARGETS CANCER STROMAL/MESENCHYMAL CELLS

(71) Applicants: MIE UNIVERSITY, Tsu (JP); KYOTO UNIVERSITY, Kyoto (JP)

(72) Inventors: Hiroshi Shiku, Tsu (JP); Naohiro Seo, Tsu (JP); Kazunari Akiyoshi, Kyoto (JP); Naozumi Harada, Tsu (JP); Fumiyasu Momose, Tsu (JP)

(73) Assignees: MIE UNIVERSITY, Tsu (JP); KYOTO UNIVERSITY, Kyoto (JP)

( * ) Notice: Subject to any disclaimer, the term of this patent is extended or adjusted under 35 U.S.C. 154(b) by 733 days.

(21) Appl. No.: 15/559,771

(22) PCT Filed: Mar. 18, 2016

(86) PCT No.: PCT/JP2016/058721
§ 371 (c)(1),
(2) Date: Feb. 28, 2018

(87) PCT Pub. No.: WO2016/152786
PCT Pub. Date: Sep. 29, 2016

(65) Prior Publication Data
US 2018/0177816 A1    Jun. 28, 2018

(30) Foreign Application Priority Data

Mar. 20, 2015 (JP) .............................. JP2015-058467

(51) Int. Cl.
| | | |
|---|---|---|
| *A61K 31/7105* | (2006.01) | |
| *A61P 35/00* | (2006.01) | |
| *A61K 35/17* | (2015.01) | |
| *C12Q 1/6876* | (2018.01) | |
| *C12N 5/0775* | (2010.01) | |
| *A61K 9/08* | (2006.01) | |
| *A61K 9/00* | (2006.01) | |
| *A61K 45/06* | (2006.01) | |

(52) U.S. Cl.
CPC ........ *A61K 31/7105* (2013.01); *A61K 9/0019* (2013.01); *A61K 9/08* (2013.01); *A61K 35/17* (2013.01); *A61K 45/06* (2013.01); *A61P 35/00* (2018.01); *C12N 5/0663* (2013.01); *C12Q 1/6876* (2013.01); *C12N 2503/02* (2013.01); *C12Q 2600/178* (2013.01)

(58) Field of Classification Search
CPC .................................................. A61K 31/7105
USPC ..................................................... 435/325
See application file for complete search history.

(56) References Cited

U.S. PATENT DOCUMENTS

2014/0031256 A1    1/2014  Lim

FOREIGN PATENT DOCUMENTS

JP        2014507140 A      3/2014

OTHER PUBLICATIONS

Okoye et al. "MicroRNA-containing T-regulatory-cell-derived exosomes suppress pathogenic T helper 1 cells." Immunity 41.1 (2014) : 89-103.*
Mittelbrunn et al. "Unidirectional transferormicroRNA-loaded exosomes from T cells to antigen-presenting cells." Nature communications 2.1 (2011): 1-10.*
Pegtel et al. "Functional delivery of viral miRNAs via exosomes." Proceedings of the National Academy of Sciences 107.14 (2010): 6328-6333 (Year: 2010).*
Mittelbrunn et al. "Unidirectional transferormicroRNA-loaded exosomes from T cells to antigen-presenting cells." Nature communications 2.1 (2011): 1-10 (Year: 2011).*
Ono et al. "Exosomes from bone marrow mesenchymal stem cells contain a microRNA that promotes dormancy in metastatic breast cancer cells." Science signaling 7.332 (2014): ra63-ra6 (Year: 2014).*
Arina A. et al. Adoptively transferred immune T cells eradicate established tumors despite cancer-induced immune suppression. J Immunol. (2014) 192: 1286-1293.
Bexell D. et al. Bone marrow multipotent mesenchymal stroma cells act as pericyte-like migratory vehicles in experimental gliomas. Mol Ther. (2009) 17: 183-190.
Boelens M. et al. Exosome transfer from stromal to breast cancer cells regulates therapy resistance pathways. Cell. (2014) 159: 499-513.
Callahan M. et al. At the bedside: CTLA-4- and PD-1-blocking antibodies in cancer immunotherapy. J. Leukoc. Biol. (2013) 94: 41-53.

(Continued)

*Primary Examiner* — James D Schultz
*Assistant Examiner* — Alexander W Nicol
(74) *Attorney, Agent, or Firm* — J-Tek Law PLLC; Jeffrey D. Tekanic; Scott T. Wakeman

(57) ABSTRACT

Therapeutic agents effective for treating cell-proliferative diseases contain extracellular vesicles (exosomes) released from cytotoxic T cells or miRNA obtained from extracellular vesicles (exosomes) released from cytotoxic T cells, such as human CD8+ T cells. Such therapeutic agents suppress the proliferation of mesenchymal cells surrounding cancer cells, e.g., by killing the mesenchymal cells, such that the cancer cells become isolated and unable to metastasize. Cell-proliferative diseases are thus treatable by administering such a therapeutic agent to a patient.

13 Claims, 22 Drawing Sheets

Specification includes a Sequence Listing.

(56) References Cited

OTHER PUBLICATIONS

Chalmin F. et al. Membrane-associated Hsp72 from tumor-derived exosomes mediates STAT3-dependent immunosuppressive function of mouse and human myeloid-derived suppressor cells. J. Clin. Invest. (2010) 120: 157-471.

Ding Z. ,et al. Chemokines stimulate human T lymphocyte transendothelial migration to utilize VLA-4 in addition to LFA-1. J Leukoc Biol. (2001) 69: 458-466.

Eikawa S. et al. Monitoring multifunctionality of immune-exhausted CD8 T cells in cancer patients. Methods Mol Biol. (2014) 1142: 11-17.

English translation of International Preliminary Report on Patentability dated Aug. 1, 2017 for parent application No. PCT/JP2016/058721.

English translation of the International Search Report dated May 17, 2016 for parent application No. PCT/JP2016/058721.

Machine English translation of Box No. V., section 2 (Citatations and Explanations) of the Written Opinion of the International Searching Authority dated May 2, 2016 for parent application No. PCT/JP2016/058721.

Filipazzi P. et al. Recent advances on the role of tumor exosomes in immunosuppression and disease progression. Semin. Cancer Biol. (2012) 22: 342-349.

Griffin M. et al. Immunological aspects of allogeneic mesenchymal stem cell therapies. Hum Gene Ther. Dec. 2010;21 (12):1641-55.

Hinrichs C. et al. Programming CD8+T cells for effective immunotherapy. Curr. Opin. lmmunol. (2006) 18: 363-370.

Houlihan D.et al. Isolation of mouse mesenchymal stem cells on the basis of expression of Sca-1 and PDGFR-alpha. Nat. Protoc. (2012) 7: 2103-2111.

Ikeda, H. et al. Mutated mitogen-activated protein kinase: a tumor rejection antigen of mouse sarcoma. Proc. Natl. Acad. Sci. USA. 94:6375-6379. 1997.

Ishihara M. et al. Systemic CD8+T cell-mediated tumoricidal effects by intratumoral treatment of oncolytic herpes simplex virus with the agonistic monoclonal antibody for murine glucocorticoid-induced tumor necrosis factor receptor. PLoS One. (2014) 9: e104669.

Joyce J. et al. Microenvironmental regulation of metastasis. Nat Rev Cancer. (2009) 9: 239-252.

Koh B. et al. The pro-metastatic role of bone marrow-derived cells: a focus on MSCs and regulatory T cells. EMBO reports. (2012) 13: 412-422.

Ly L. et al. Effective cooperation of monoclonal antibody and peptide vaccine for the treatment of mouse melanoma. J Immunol. (2013) 190: 489-496.

Maciag P. et al. Cancer immunotherapy targeting the high molecular weight melanoma-associated antigen protein results in a broad antitumor response and reduction of pericytes in the tumor vasculature. Cancer Res. (2008) 68: 8066-8075.

McDonald D. et al. Significance of Blood Vessel Leakiness in Cancer. Cancer Res. (2002) 62: 5381-5385.

Mi Z. et al. Osteopontin promotes CCL5-mesenchymal stromal cell-mediated breast cancer metastasis. Carcinogenesis. (2011) 32: 477-487.

Momose F., et al. Guanine-rich sequences are a Dominant Feature of Exosomal microRNAs across the Mammalian Species and Cell Types, PLOS ONE (2016), 11(4), Apr. 21, 2016.

Montecalvo, Angela, et al., "Methods of Purification of CTL-Derived Exosomes," Methods in Molecular Biology, 2014, vol. 1186, pp. 87-102.

Nandi A. et al. Bimolecular complex between Rolling and Firm Adhesion Receptors Required for Cell Arrest: CD44 Association with VLA-4 in T Cell Extravasation. Immunity. (2004) 20: 455-465.

Naohiro S., et al. Activated CD8+ T cell extracellular vesicles prevent tumour progression by targeting of lesional mesenchymal cells. Nature Communications. (2018)9:435, DOI: 10.1038/s41467-018-02865-1. Published online Jan. 30, 2018.

Nieto M. et al. The epithelial-mesenchymal transition under control: Global programs to regulate epithelial plasticity. Semin. Cancer Biol. (2012) 22: 361-368.

Nieto M. The Ins and Outs of the Epithelial to Mesenchymal Transition in Health and Disease. Annu. Rev. Cell Dev. Biol. (2011) 27:347-376.

Ochs K. et al. Immature mesenchymal stem cell-like pericytes as mediators of immunosuppression in human malignant glioma. J Neuroimmunol. (2013) 265: 106-116.

Ono M.et al. Exosomes from bone marrow mesenchymal stem cells contain a microRNA that promotes dormancy in metastatic breast cancer cells. Sci Signal. (2014) 7:332 ra63, 1-10.

Prakash M. et al. Granzyme B promotes Cytotoxic Lymphocyte Transmigration via Basement Membrane Remodeling. Immunity. (2014) 41: 960-972.

Pucci F. et al. Molecular Pathways: Tumor-derived microvesicles and their interactions with immune cells in vivo. Clin. Cancer Res. (2013) 19: 2598-2604.

Roccaro A. et al. BM mesenchymal stromal cell-derived exosomes facilitate multiple myeloma progression. J Clin Invest. (2013) 123: 1542-1555.

Seo, N., et al., "Tumor- and Immune Cell-Derived Exosomes," Drug Delivery System, 2014, vol. 29, No. 2, pp. 152-159.

Shimada M. et al. Apoptosis of antigen-specific CTLs contributes to low immune response in gut-associated lymphoid tissue post vaccination. Vaccine. (2014) 32: 5198-5205.

Shimoda M. et al. Loss of the Timp gene family is sufficient for the acquisition of the CAF-like cell state. Nat. Cell Biol. (2014)16: 889-901.

Stauss H. et al. Immunotherapy with gene-modified T cells: limiting side effects provides new challenges. Gene Ther. (2013) 20: 1029-1032.

Tran E. et al. Immune targeting of fibroblast activation protein triggers recognition of multipotent bone marrow stromal mils and cachexia. J Exp Med. (2013) 210: 1125-1135.

Vajkoczy P. et al. Multistep Nature of Microvascular Recruitment of Ex Vivo-expanded Embryonic Endothelial Progenitor Cells during Tumor Angiogenesis. J. Exp. Med. (2003) 197: 1755-1765.

Webber J. et al. Cancer Exosomes Trigger Fibroblast to Myofibroblast Differentiation. Cancer Res. (2010) 70: 9621-9630.

Winograd R. et al. Induction of T cell immunity overcomes complete resistance to PD-1 and CTLA-4 blockade and improves survival in pancreatic carcinoma. Cancer Immunol Res. (2015) Published OnlineFirst Feb. 12, 2015; DOI: 10.1158/2326-6066.CIR-14-0215, 3(4) Apr. 2015, 399-411.

Yoong K. et al. Vascular Adhesion Protein-1 and ICAM-1 Support the Adhesion of Tumor-Infiltrating Lymphocytes to Tumor Endothelium in Human Hepatocellular Carcinoma. J Immunol. (1998) 160: 3978-3988.

Sato Y., et al. Engineering hybrid exosomes by membrane fusion with liposomes. Scientific Reports, 6:21933, DOI: 10.1038/srep21933, Published: Feb. 26, 2016.

* cited by examiner

A

| | DUC18 ECV No.1 | DUC18 ECV No.2 | DUC18 ECV No.3 |
|---|---|---|---|
| Protein conc. | 292 μg/400 mL | 556 μg/750 mL | 2028 μg/2 L |
| No. of particles | $33.54 \times 10^{11}$ | $21.93 \times 10^{11}$ | $4.716 \times 10^{12}$ |

(nm)

| | BALB/c ECV | CMS5aTB ECV | hPBMC ECV |
|---|---|---|---|
| Protein conc. | 200 μg/350 ml | 458 μg/500 ml | 510 μg/500 ml |
| No. of particles | $18.21 \times 10^{11}$ | $15.28 \times 10^{11}$ | $23.56 \times 10^{11}$ |

(nm)

B

DUC18 ECV      CMS5aTB ECV

Top 11 of the up-regulated mRNAs in both B6 and CMS5a tumors in contact with BM-MSCs.

FIG. 15

| miRNA name | DUC18 ECV | BALB/c ECV | CMS5aTB ECV | CD4 BALB/c ECV |
|---|---|---|---|---|
| miR-298-5p | 254.3 | 147.0 | 79.3 | 94.5 |
| miR-351-5p | 192.7 | 86.2 | 87.0 | 85.7 |
| miR-700-3p | 169.4 | 58.5 | 69.7 | 48.2 |
| miR-1943-5p | 295.0 | 107.5 | 77.3 | 112.5 |
| miR-1249-5p | 1076.1 | 879.2 | 571.4 | 717.3 |
| miR-370-5p | 118.3 | 32.2 | 39.4 | 49.8 |
| mmiR-6392-5p | 114.4 | 68.0 | 55.5 | 71.0 |
| miR-5099 | 1476.8 | 475.4 | 163.7 | 1198.3 |

DUC18 ECV dominant miRNAs selected by the comparison with CMS5a, BALB/c, and CD4 BALB/c miRNAs

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial
<220> FEATURE:
<223> OTHER INFORMATION: mERK2 136-144

<400> SEQUENCE: 1

Gln Tyr Ile His Ser Ala Asn Val Leu
1               5

<210> SEQ ID NO 2
<211> LENGTH: 9
<212> TYPE: PRT
<213> ORGANISM: Artificial
<220> FEATURE:
<223> OTHER INFORMATION: TRP-2

<400> SEQUENCE: 2

Ser Val Tyr Asp Phe Phe Val Trp Leu
1               5

<210> SEQ ID NO 3
<211> LENGTH: 9
<212> TYPE: PRT
<213> ORGANISM: Artificial
<220> FEATURE:
<223> OTHER INFORMATION: gp100

<400> SEQUENCE: 3

Glu Gly Ser Arg Asn Gln Asp Trp Leu
1               5
```

```
<210> SEQ ID NO 4
<211> LENGTH: 23
<212> TYPE: RNA
<213> ORGANISM: Artificial
<220> FEATURE:
<223> OTHER INFORMATION: m-miR298-5p

<400> SEQUENCE: 4
ggcagaggag ggcuguucuu ccc                                              23

<210> SEQ ID NO 5
<211> LENGTH: 22
<212> TYPE: RNA
<213> ORGANISM: Artificial
<220> FEATURE:
<223> OTHER INFORMATION: m-miR-298-3p

<400> SEQUENCE: 5
gaggaacuag ccuucucuca gc                                               22

<210> SEQ ID NO 6
<211> LENGTH: 23
<212> TYPE: RNA
<213> ORGANISM: Artificial
<220> FEATURE:
<223> OTHER INFORMATION: m-miR-1943-5p

<400> SEQUENCE: 6
aagggaggau cugggcaccu gga                                              23

<210> SEQ ID NO 7
<211> LENGTH: 21
<212> TYPE: RNA
<213> ORGANISM: Artificial
<220> FEATURE:
<223> OTHER INFORMATION: m-miR-1943-3p

<400> SEQUENCE: 7
caggugccag cuccucccuu c                                                21

<210> SEQ ID NO 8
<211> LENGTH: 22
<212> TYPE: RNA
<213> ORGANISM: Artificial
<220> FEATURE:
<223> OTHER INFORMATION: m-miR-5099-5p

<400> SEQUENCE: 8
guuagaaauu acauugauuu aa                                               22

<210> SEQ ID NO 9
<211> LENGTH: 20
<212> TYPE: RNA
<213> ORGANISM: Artificial
<220> FEATURE:
<223> OTHER INFORMATION: m-miR-5099-3p

<400> SEQUENCE: 9
uuagaucgau guggugcucc                                                  20

<210> SEQ ID NO 10
<211> LENGTH: 22
<212> TYPE: RNA
<213> ORGANISM: Artificial
<220> FEATURE:
<223> OTHER INFORMATION: m-miR-150-5p
```

```
<400> SEQUENCE: 10
ucucccaacc cuuguaccag ug                                              22

<210> SEQ ID NO 11
<211> LENGTH: 22
<212> TYPE: RNA
<213> ORGANISM: Artificial
<220> FEATURE:
<223> OTHER INFORMATION: m-miR-150-3p

<400> SEQUENCE: 11
cugguacagg ccuggggau ag                                               22

<210> SEQ ID NO 12
<211> LENGTH: 23
<212> TYPE: RNA
<213> ORGANISM: Artificial
<220> FEATURE:
<223> OTHER INFORMATION: m-miR-223-5p

<400> SEQUENCE: 12
cguguauuug acaagcugag uug                                             23

<210> SEQ ID NO 13
<211> LENGTH: 22
<212> TYPE: RNA
<213> ORGANISM: Artificial
<220> FEATURE:
<223> OTHER INFORMATION: m-miR-223-3p

<400> SEQUENCE: 13
ugucaguuug ucaaauaccc ca                                              22

<210> SEQ ID NO 14
<211> LENGTH: 21
<212> TYPE: RNA
<213> ORGANISM: Artificial
<220> FEATURE:
<223> OTHER INFORMATION: m-miR-3470b-5p

<400> SEQUENCE: 14
ucacucugua gaccaggcug g                                               21

<210> SEQ ID NO 15
<211> LENGTH: 18
<212> TYPE: RNA
<213> ORGANISM: Artificial
<220> FEATURE:
<223> OTHER INFORMATION: m-miR-3470b-3p

<400> SEQUENCE: 15
ccugccucug ccucccga                                                   18
```

THERAPEUTIC AGENT ASSOCIATED WITH SUPPRESSION OF PROLIFERATION AND METASTASIS OF TUMOR, WHICH COMPRISES EXOSOMES RELEASED FROM CYTOTOXIC T CELLS AND TARGETS CANCER STROMAL/MESENCHYMAL CELLS

CROSS-REFERENCE

This application is the US national stage of International Patent Application No. PCT/JP2016/058721 filed on Mar. 18, 2016, which claims priority to Japanese Patent Application No. 2015-058467 filed on Mar. 20, 2015.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
| --- | --- | --- |
| MIE006_Seq_List.txt | Feb. 23, 2018 | 3 |

Technical Field

The present invention generally relates to a therapeutic agent for treating cell-proliferative diseases such as cancers, in which exosomes released from cytotoxic T cells or miRNA contained in the exosomes serve as an active ingredient.

Background Art

In primary tumor tissues, tumor-associated stroma is formed by extracellular matrices made of fibronectin, laminin, collagen, etc., and many types of other cells. These cells include tumor-associated fibroblasts (CAFs; fibroblast markers and platelet-derived growth factor receptor α (CD140a)$^+$, α smooth muscle actin (α-SMA)$^+$) and mesenchymal stem cells (MSCs) (see Non Patent Literature 1. The references are listed at the end of the specification): CD140a$^+$, stem cell antigen (Sca-1)$^+$). In addition, when cancer cells are rigidly adhered to each other by E-cadherin, etc. (Non Patent Literature 3 and 4), gaps between the cancer cells are filled by growing stromal cells, and angiogenesis occurs there (Sca-1$^+$CD31$^+$) (Non Patent Literature 2). Malignant transformation of the cancer cells, exemplified by the epithelial to mesenchymal transition (EMT) by interaction with the stromal cells, plays an important role in the invasion and metastasis of tumors. The epithelial to mesenchymal transition can be a marker for determining the malignant transformation of a tumor (Non Patent Literature 5). There are several reports concerning molecules responsible for the epithelial to mesenchymal transition (Non Patent Literature 3, 6, and 7).

Endosomal membrane-derived microvesicles (having diameters of 100 nm to 200 nm) are released from many types of cells, including tumor cells and tumor-associated stromal cells, and the proteins and RNA contained therein mediate cell-cell signaling (Non Patent Literature 8 and 9).

Tumor cells release a variety of extracellular vesicles (ECVs) (sometimes referred to as exosomes, and will be called "exosomes" or "ECVs" herein) that have been reported to be responsible for self-proliferation, immune tolerance, modification of the tumor environment, etc. (Non Patent Literature 8, and 10 to 13). On the other hand, there are also reports that exosomes released from tumors promote epithelial to mesenchymal transitions, expansions, and aggravations of tumors (Non Patent Literature 9, 14, and 15). Accordingly, research of exosomes has become important for evaluating the aggravation of tumors.

According to mouse model and human studies, activated tumor-invading CD8$^+$ T cells seem to invade tumors and tumor-associated stroma (Non Patent Literature 16). Furthermore, in immunotherapies using monoclonal antibodies against tumor-associated antigens, CD8$^+$ T cells (including cytotoxic T-lymphocytes (CTL)) accumulate or proliferate in tumor tissues (Non Patent Literature 17 and 18). Because CTLs, which are not tumor specific, invade tumors from the blood vessels by remodeling basement membranes (Non Patent Literature 19), CD8$^+$ T cells are presumed to be involved in tumor growth and aggravation in various ways.

Summary

To date, however, little is known about exosomes released from cytotoxic T cells with regard to what role they play in the malignant transformation of tumors and under what conditions.

Therefore, the present inventors have investigated in detail the effects of exosomes released from cytotoxic T cells on the malignant transformation of tumors. As a result, we observed that, among the various cytotoxic T cells, exosomes derived from CD8$^+$ T cells, in particular, kill mesenchymal cells surrounding the tumor tissue, not the cancerous portion of the tumor tissue, and suppress the progression of cancer, including the proliferation and metastasis of the cancer.

Therefore, a first aspect of the present teachings relates to a therapeutic agent for cell-proliferative diseases, the therapeutic agent including extracellular vesicles (exosomes) released from cytotoxic T cells.

A second aspect of the present teachings relates to the therapeutic agent for cell-proliferative diseases according to the first aspect, which includes extracellular vesicles (exosomes) released from at least one of human CD4$^+$, CD8$^+$, CD9$^+$, CD63$^+$, and TCR$^+$ T cells from among the cytotoxic T cells.

A third aspect of the present teachings relates to the therapeutic agent for cell-proliferative diseases according to the second aspect, which includes extracellular vesicles (exosomes) that are extracellular vesicles (exosomes) released from CD8$^+$ T cells from among the cytotoxic T cells.

A fourth aspect of the present teachings relates to the therapeutic agent for cell-proliferative diseases according to the second or the third aspect, in which the extracellular vesicles (exosomes) contain miRNA that is effective in suppressing cell proliferation.

A fifth aspect of the present teachings relates to the therapeutic agent for cell-proliferative diseases according to the fourth aspect, the therapeutic agent including the miRNA that is effective in suppressing cell proliferation.

A sixth aspect of the present teachings relates to the therapeutic agent for cell-proliferative diseases according to the second aspect, the therapeutic agent further including one or more selected from microbicides, mucolytic agents, tonicity-adjusting agents, pH control agents, stabilizing agents, thickening agents, preservatives, adhesives, and immunostimulating agents.

A seventh aspect of the present teachings relates to the therapeutic agent for cell-proliferative diseases according to the second aspect, the therapeutic agent being injected, intravenously or subcutaneously, into tumor tissue, or into mesenchymal cells within tumor tissue.

An eighth aspect of the present teachings relates to a method of extracting miRNA for treating cell-proliferative diseases, the method including collecting exosomes released from cytotoxic T cells; and identifying miRNA that is effective in suppressing cell proliferation from those exosomes.

A ninth aspect of the present teachings relates to a therapeutic agent for cell-proliferative diseases, the therapeutic agent including miRNA that is effective in suppressing cell proliferation.

A tenth aspect of the present teachings relates to a method of identifying MSC cytotoxic miRNA, the method including adding miRNA having a base sequence that is same as a base sequence of miRNA contained in exosomes released from cytotoxic T cells to cultured human mesenchymal stem cells (MSCs), culturing the MSC, and investigating toxic activity against the MSC to evaluate the MSC cytotoxicity of the miRNA.

Once MSC cytotoxic miRNA is identified, exosomes containing the miRNA or miRNA having a sequence same as the sequence of the identified miRNA are synthesized, and it (they) is (are) used as a therapeutic agent for cell-proliferative disorders by reconstituting the resulting miRNA as is or in an exosome-like manner. Thus, an eleventh aspect of the present teachings relates to a therapeutic agent for cell-proliferative diseases, the therapeutic agent including MSC cytotoxic miRNA.

Another aspect relates to a method for treating cell-proliferative diseases, the method including administering the therapeutic agent of any of the aspects described above to a patient. The administration method is preferably any of an intratumoral method into tumor tissue, an intracellular method into mesenchymal cells within tumor tissue, an intravenous method or a subcutaneous method.

"Exosomes" refer to vesicles that are composed of a lipid bilayer membrane, are externally secreted from a variety of cells, and have a diameter of about 40 nm to 200 nm. Exosomes can be observed in vivo in body fluids such as saliva, blood, urine, amniotic fluids, and malignant ascites. In addition, exosomes are secreted from culture cells into the culture media. A variety of proteins and RNA are contained in exosomes, and they have been thought to mediate cell-cell signaling.

Moreover, according to the present teachings, by administering exosomes obtained from cytotoxic T cells, the exosomes kill mesenchymal cells surrounding cancer cells (cancer stromal disintegration) so that proliferation/metastasis of the cancer cells can be suppressed. Among such cytotoxic T cells, exosomes derived from CD8$^+$ T cells are particularly effective in suppressing proliferation/metastasis. As a mechanism of action, the exosomes are taken up into both cancer cells and mesenchymal cells, but only the mesenchymal cells die (apoptosis); as a result, proliferation/metastasis of cancer cells is suppressed because stromal cells, which are necessary for the proliferation and metastasis of cancer cells, are lost and the cancer cells are isolated. In addition, the suppressive effects on the proliferation/metastasis of cancer cells can similarly be observed even by using specific miRNA contained in the exosomes.

Thus, according to one aspect of the present teachings, a therapeutic agent for cell-proliferative diseases includes extracellular vesicles (exosomes) derived from cytotoxic T cells that serve as an active ingredient. In another aspect of the present teachings, a therapeutic agent for cell-proliferative diseases includes miRNA that is effective in suppressing cell proliferation. Such therapeutic agents can suppress cell proliferation and metastasis of tumors such as cancer.

BRIEF DESCRIPTION OF THE FIGURES

FIG. 1A shows five graphs that depict the results of flow cytometry analyses of 4 day-cultured splenocytes obtained from DUC18 mice, CMS5a-inoculated BALB/c mice, BALB/c mice, and CD8$^+$ T cell deficient BALB/c mice, as well as hPBMC, using CD4-, CD8-, and TCRαβ-specific monoclonal antibodies for mice and humans. FIG. 1B shows five graphs that depict the results of flow cytometry analyses of DUC18 ECV-immobilized latex beads that were all stained with a control monoclonal antibody, and were respectively stained with a CD4-specific monoclonal antibody, a CD8-specific monoclonal antibody, a TCRVb-specific monoclonal antibody, a CD9-specific monoclonal antibody, and a CD63-specific monoclonal antibody. FIG. 1C shows two graphs that depict tumor growth and were prepared as follows: CMS5a was inoculated into wild type mice and BALB/c nude mice. On day 12 after the inoculation of CMS5a, ECVs derived from DUC18, CMS5a TB and BLAB/c mice, respectively, were intratumorally injected into the wild type mice and BALB/c nude mice (The symbols in the graphs indicate the following: *<0.05, **<0.001, n.s.: no significant difference). FIG. 1D shows three micrographs of spheroid formations that were prepared as follows: On day 3 after the ECV treatments, suspensions of CMS5a tumors were prepared. The micrographs were taken after culturing the suspensions for 24 hours. FIG. 1E shows four fluorescence micrographs of CMS5a tumor sections on day 3 after the ECV treatments. The sections were stained with a Ki-67 monoclonal antibody and DAPI.

FIG. 3A shows ECVs derived from DUC18 (Lot Nos. 1, 2 and 2), ECVs derived from BALB/c, ECVs derived from CMS5a TB, and ECVs derived from hPBMC, which were measured for total protein concentration (numerical values) by the BCA assay, and for the total number (numerical values) and average diameter (graphed data) by the NTA assay. FIG. 3B shows electron micrographs of a DUC18 ECV and a CMS5a ECV.

FIG. 4A shows (top view) a timeline, which indicates that on day 10 after BALB/c mice were inoculated with CT26, DUC18 ECVs were intratumorally injected into the CT26-inoculated BALB/c mice, and (bottom view) the tumor diameters that were observed on days 10, 17, 21 and 23. FIG. 4B graphically shows the flow cytometry analysis of CT26 tumor cells that were co-cultured with cultured BM-MSC in the presence or absence of DUC18 ECV, with respect to the expression of CD140a. FIG. 4C shows micrographs of spheroid formations of CT26 tumor cells that were co-cultured with cultured BM-MSC in the presence of DUC18 ECVs or with CMS5a TB ECVs.

FIG. 6C shows four fluorescence micrographs of CMS5a tumor sections on day 3 after the ECV treatments. The sections were stained with a CD140a specific monoclonal antibody and DAPI. FIG. 6D shows the results of a flow cytometry analysis concerning CD140a expression in the tumor cells, which were prepared as follows: ECVs prepared from culture media of B6 splenocytes stimulated with TRP-2 and gp100 peptides (day 5, day 7, day 10, or day 15) were intratumorally injected into CMS5a-inoculated BALB/c mice and B16-inoculated B6 mice, respectively, on day 12 after the tumor inoculations. On day 3 after the ECV injection, suspensions of the tumor cells were stained with a CD140a specific monoclonal antibody, and the CD140a expression of the tumor cells was determined.

FIG. 8A shows graphs of a flow cytometry analysis of CD140a expression in tumors grown by adding DUC18 EVCs (Lots 1 and 2), BALB/c ECVs, and CMS5a TB ECVs, respectively, to culture media of CMD5a, CT26, 4T1, CMS7, and CMS5m, respectively. On day 3 after the addition, CD140a expression was determined. A rat IgG2a monoclonal antibody was used as a control. FIG. 8B shows a flow cytometry analysis of an annexin V monoclonal antibody, which was prepared as follows: DUC18 ECVs and BLAB/c ECVs, respectively, were added to culture media of CT26, CMS5a, 4T1, and CMS7, respectively. On day 3 after the addition, each of the tumor cells was stained with the annexin V monoclonal antibody, and analyzed by flow cytometry.

FIG. 9A shows nine fluorescence micrographs of sections obtained from CMS5a tumors on day 3 after intratumoral injections of DUC18 ECV or CMS5a TB ECV. The sections were stained with a CD140a specific monoclonal antibody, an Sca-1 specific monoclonal antibody, and DAPI to evaluate tumor proliferation and stromal stem cells (MSCs); stained with an ER-TR7 specific monoclonal antibody, an α-SMA specific monoclonal antibody, and DAPI to evaluate cancer-associate fibroblasts (CAFs); and stained with a TGF-β1 specific monoclonal antibody, an Sca-1 specific monoclonal antibody, and DAPI to evaluate epithelial to mesenchymal transition (EMT) of the tumor. FIG. 9B shows six graphs of a flow cytometry analysis, which were prepared as follows: Cells obtained from crushed femurs were cultured for 1 month to prepare BM-MSC. DUC18 ECVs, B6 ECVs, and hPBMC ECVs, respectively, were added to BM-MSC culture media at the concentrations illustrated in FIG. 9B. BM-MSC that were remaining after 3 days were stained with the annexin V monoclonal antibody, and the total number was counted by flow cytometry. FIG. 9C shows graphs of CD140 expression (left side) and spheroid formation (right side). More specifically, DUC18 ECVs were added to CMS5a and B16, respectively, co-cultured with MSC at the concentrations illustrated in FIG. 9C, and cultured for 4 days. The resulting tumor cells were stained with a CD140a specific monoclonal antibody, and analyzed by flow cytometry (left side graph). The number of spheroids was determined under microscope for each of CMS5a, 4T1, CT26, and B16, to which DUC18 ECVs and CMS5a TB ECVs, respectively, were added and cultured with MSC (Each of the symbols in the graphs indicate the following: *<0.05, **<0.001, n.s.: no significant difference). FIG. 9D graphically shows the results of a flow cytometry analysis that were prepared as follows: $CD90.1^+$ BM-MSC chimera mice were prepared by transferring normal BM cells of BLAB/c mice and cultured $CD90.1^+$ BM-MSC into irradiated BALB/c mice. In month 2 after the $CD90.1^+$ BM-MSC were transferred, DUC18 ECVs, hPBMC ECVs, and BLAB/c ECVs, respectively, were injected into CMS5a tumors on day 12 after inoculation thereof. On day 3 after the ECV treatment, percentages of CD140a and Sca-1 positive cells and CD90.1 expression were analyzed by flow cytometry.

FIG. 10B shows a photograph of Giemsa staining to determine colony formation of BM-MSC after culturing for 2 weeks. FIG. 10C shows photographs of BM-MSC differentiated into adipocytes or osteocytes with staining using Oil Red O and Alizarin Red S, respectively. The adipocytes and osteocytes were grown by culturing the BM-MSC for 1 month (about 80% confluent) and then further culturing in an adipogenic medium or an osteogenic medium for 3 weeks to induce differentiation.

FIG. 12B graphically shows the results of a flow cytometry analysis that was performed as follows: B16 and CMS5a tumor suspensions were prepared 30 minutes after SYTO RNASelect-stained DUC18 ECVs were added, and the suspensions were stained with CD140a, Sca-1 specific monoclonal antibodies, and analyzed by flow cytometry as illustrated in the graphs. FIG. 12C shows two fluorescence microscope photographs of sections that were prepared from tumors 30 minutes after the SYTO RNASelect-stained DUC18 ECVs were injected. The sections were stained with a CD140a specific monoclonal antibody and DAPI, or with a Sca-1 specific monoclonal antibody and DAPI.

FIG. 13B shows a table listing the top 9 genes whose expressions were increased in both B16 and CMS5a tumors co-cultured with BM-MSC.

FIG. 14A shows the results that were generated in the following manner: miRNA was obtained from ECVs released from BALB/c, CMS5a TB, and CD4 BALB/c, and compared to select miRNA dominant in DUC18 ECVs. The selected 15 miRNA genetically form 2 clusters. miR-298, miR-1943, and miR-5099 exhibited higher amounts of expression, and were obtained from those unknown in PubMed®. FIG. 14B shows a pie graph that was prepared as follows: miR-351, -700, -1943, -344g, -1199, -5113, -5114, -6347, -6392, and -5099 were not known in a PubMed® search in the fields of tumor, cancer, immune system, invasion or metastasis. miR-298, -141, -1249, -23b, and -370 have been reported to be involved in tumor proliferation and immune activation, as well as tumor proliferation and immunostimulation. As illustrated in the pie graph, 70% of existing reports regarding the selected DUC18 ECV dominant miRNA concerned the downregulation of tumor promotion and proliferation. From this, our search method was found to be accurate. FIG. 14C graphically shows the results of a flow cytometry analysis that was performed as follows: The selected miR-298, -1943, and -5099 were synthesized, and were transfected into cultured BM-MSC individually or as mixed. Negative control miR and synthesized CMS5a TB ECV dominant miR (miR-150, -223, or -3470b) were used as controls. On day 3 after the transfection, the total number of remaining BM-MSC was counted by flow cytometry as illustrated in the two graphs.

FIG. 15 is a chart that shows fourteen miRNA, which are dominant in DUC18 ECV and were selected by comparing with BLAB/c, CMS5a TB, or CD4 BALB/c miRNA. miRNA having 100 indicators or more, extracted by global normalization, are indicated in shading. Three miRNAs indicated in gray shading in the left-side column (i.e. miR-298-5p, miR-1943-5p, and miR-5099) were used for studying BM-MSC depletion.

FIG. 16A is a timeline diagram illustrating time points of sequentially observing the invasion and lung metastasis of B16F10 after B16F10 melanoma cells were subcutaneously injected into B6 mice. On day 10, day 13, and day 16 after the tumor injection, DUC18 ECVs or BALB/c ECVs were injected into primary B16F10 tumors at 50 μg/tumor/site. FIG. 16B shows two representative micrographs of 6 tumors in the untreated group that were prepared as follows: On day 18 after the tumor injection, B16F10 tumors were removed, and invasion was investigated by using HE staining. FIG. 16C shows representative fluorescence micrographs of 3 samples in each group that were prepared as follows: On day 18 after the tumor injection, sections of the B16F10 tumors were prepared, and stained with CD140a, Sca-1 and DAPI.

FIG. 17A is a graph that shows the results of the total protein concentrations, as measured by the BSA method, of the ECVs obtained from CD90.1 DUC18 CD8$^+$ T cells cultured in DMSO (untreated) or in a GW4869 treatment. FIG. 17B shows four fluorescence micrographs that were prepared as follows: CD90.1 DUC18 CD8$^+$ T cells treated with DMSO or GW4869 were intravenously injected into BALB/c mice on day 12 after CMS5a inoculation. After 24 hours, sections of the resulting tumors were prepared. The fluorescence micrographs show the sections stained with a CD90.1 monoclonal antibody, an Sca-1 monoclonal antibody, and DAPI, or a CD31 monoclonal antibody, an Sca-1 monoclonal antibody, and DAPI. FIG. 17C depicts additional fluorescence micrographs that were prepared as follows: The CMS5a tumor was inoculated into BALB/c wild type and nude mice, respectively. On day 12 after the inoculation, CD90.1 DUC18 CD8$^+$ T cells treated with DMSO or GW4869 were injected into these mice. On day 1, day 2, day 3, day 5, and day 7 after the injection, sections of the tumors were prepared. The fluorescence micrographs depict the sections stained with a CD90.1 monoclonal antibody, an Sca-1 monoclonal antibody, and DAPI, or a CD140a monoclonal antibody, an Sca-1 monoclonal antibody, and DAPI.

FIG. 18A graphically shows the results of a flow cytometry analysis that was performed as follows: ECVs obtained from culture supernatants of CD90.1 DUC18 CD8+ T cells were immobilized on latex beads, and stained with a control monoclonal antibody, a CD8 monoclonal antibody, a CD9 monoclonal antibody, or a CD90.1 monoclonal antibody for analysis by flow cytometry. FIG. 18B contains six fluorescence micrographs that show sections of the tumors, which were obtained 24 hours after injection of GW4869-treated or untreated CD90.1 DUC18 CD8+ T cells, stained with a CD90.1 (Thy-1.1) monoclonal antibody and DAPI; a CD8 monoclonal antibody, a CD90.1 monoclonal antibody, and DAPI; or a CD8 monoclonal antibody, a CD9 monoclonal antibody, and DAPI. FIG. 18C depicts representative focal points from 6 photographs that were prepared as follows: Sections of the tumors, which were obtained 24 hours after injection of GW4869-treated or untreated CD90.1 DUC18 CD8+ T cells, and then stained with an FITC-conjugated CD90.1 (Thy-1.1) monoclonal antibody, a PE-conjugated CD140a monoclonal antibody, and an APC-conjugated Sca-1 monoclonal antibody, and DAPI, were observed under a 2 photon confocal microscope. The MSC areas are circled with dots, arrows indicate CD90.1 DUC18 CD8+ T cells invaded into the tumor, and arrows indicate CD140a+ Sca-1+ MSC uptaking CD90.1 ECV.

DETAILED DESCRIPTION

Figure 1:
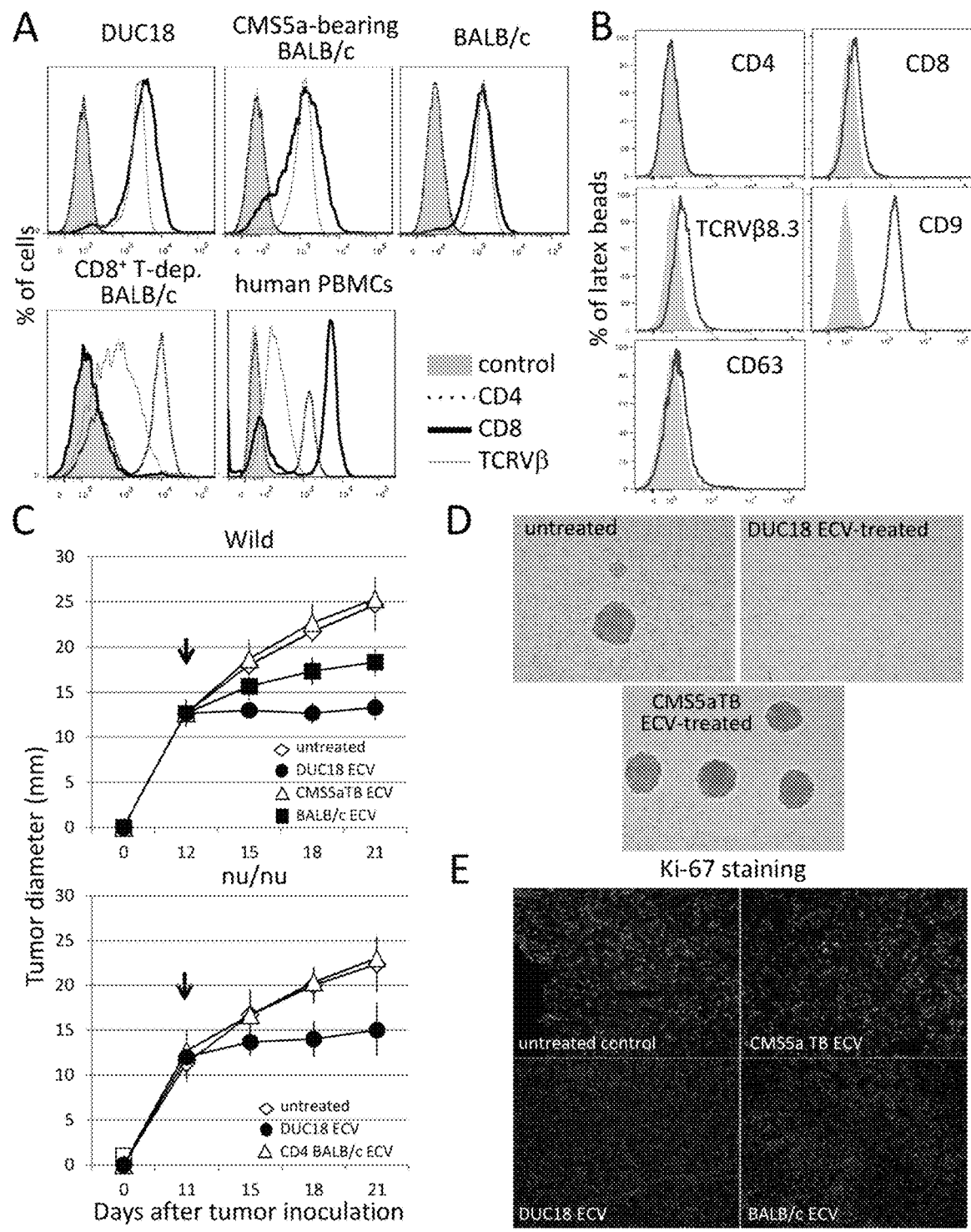
FIGS. 1A-1E concern the suppressive effects of tumor proliferation induced by intratumoral administration of ECVs released from CD8$^+$ T cells. More specifically.

Next, embodiments of the present teachings will be explained in further detail with reference to the drawings and tables. The scope of the present invention is not limited to these embodiments, and a variety of other embodiments will be possible without departing from the gist of the present invention.

Therapeutic agents according to the present teachings include extracellular vesicles (exosomes) released from cytotoxic T cells serving as an active ingredient. The cytotoxic T cells may be obtained from humans, monkeys, mice, rats, cattle, horses, camels, sheep, or birds (including chickens and ostriches). Note that the cytotoxic T cells used for treatments are not necessarily obtained from the same species; however, cytotoxic T cells obtained from the same species are preferably used. In addition, even in cases where cytotoxic T cells obtained from the same species are used, the cytotoxic T cells are not necessarily limited to those obtained from the subject to be treated (including humans, and animals other than humans), and the therapeutic agent may be extracted from cytotoxic T cells of other individuals.

Although the therapeutic agents include extracellular vesicles (exosomes) released from the cytotoxic T cells, which are at least 1, or 2 or more of CD4+, CD8+, CD9+, CD63+, and TCR+ T cells, the cytotoxic T cells are not limited thereto.

"Cell-proliferative disease" refers to diseases having a characteristic in that cells abnormally proliferate beyond the normal range, and examples thereof include malignant tumors (cancers), and precancerous conditions (conditions where the risks of malignant tumors are significantly increased, or precancerous lesions with morphological alterations that easily induce malignant tumors as compared to normal tissues).

Furthermore, the therapeutic agents are effective for not only suppression of cell proliferation, but also suppression of metastases. In addition, although the effective targets of the therapeutic agent are preferably tumors from precancerous conditions to cancerous conditions, the therapeutic agents are effective for suppression of proliferation and metastases of any tumors regardless of whether they are benign or malignant.

Methods for administrating a therapeutic agent of the present teachings include, without limitation, direct injection into tumors, injection into mesenchymal cells surrounding a tumor, intravenous injection, and subcutaneous injection.

Moreover, therapeutic agents according to the present teachings include miRNA derived from extracellular vesicles (exosomes), which were released from cytotoxic T cells, serving as an active ingredient. The miRNA preferably exhibits activity effective in suppressing cell proliferation.

"miRNA" (micro RNA) means one type of ncRNA (non-coding RNA), which is found inside cells, is a short RNA having a length of about 20 to 25 bases, and is thought to have the function of regulating gene expression.

In addition, such miRNA can be used by being encapsulated in endoplasmic reticulum (exosomes, including artificial liposomes).

In addition, examples of the additives listed in the sixth aspect of the present teachings, that is, microbicides, tonicity-adjusting agents, pH control agents, stabilizing agents, thickening agents, preservatives, fragrances, adhesives, and immunostimulating agents, are mentioned below. Specific examples of the microbicides include iodine preparations and alcohols. Pronase is a specific example of a mucolytic agent. Specific examples of the tonicity-adjusting agents include sodium chloride and glycerin. Specific examples of the pH control agents include citric acid, gluconic acid, succinic acid, potassium carbonate, and lactic acid. Specific examples of the stabilizing agents and the thickening agents include carrageenan, sodium carboxymethyl cellulose, xanthan gum, guar gum, and pectin. A specific example of the preservative (preservation agents) includes benzoic acid. Specific examples of the adhesives include gelatin, starch, and casein. Specific examples of the immunostimulating agents include agonists of Toll-like receptors, such as CpG oligo DNA and poly IC RNA, chemotherapeutics, such as taxane compounds, and signaling inhibitors. These examples do not indicate limitations, and any substances can be used as long as they are safe to living cells.

Test Methods

1. Mice and Tumor Cell Lines 6-8 week old BALB/c (CD90.2) and C57BL/6 (B6) female mice were purchased from Japan SLC. CD90.1 congenic BALB/c mice, H-2Kd-restricted and mutated ERK2 (mERK2) 136-144 (SEQ ID 1: QYIHSANVL) peptide-specific TCR (Vβ10.1/Jβ48 and Vβ8.3/Dβ2.1/Jβ2.6) gene-transfected DUC18 mice (Non Patent Literature 20) and CD90.1 congenic DUC18 mice were maintained in the Experimental Animal Facility of Mie University. CMS5a, CMS7, CT26, 4T1, B16, and B16F10 tumor cell lines were passaged using D-MEM medium containing 10% FCS. CD8$^+$ T cells obtained by culturing DUC18 mouse splenocytes specifically lysed mREK2$^+$ CMS5a, but did not lyse mREK2$^-$ CMS7, CT26 (to BALB/c background), B16 or B16F10 melanoma (to B6 background). The experimental protocol was evaluated by the Animal Care and Use Committee of Mie University.

2. Preparation of Extracellular Microvesicles (ECVs) from Culture Media

FCS was ultracentrifuged at 100,000×g for 4 hours, and then filtered (0.45 μm and 0.22 μm) to prepare FCS not containing ECV (ECV-free FCS). Splenocytes prepared from DUC18 mice and CD90.1 DUC18 mice (2×10$^7$/ml) were respectively cultured in RPMI-1640 medium containing 10% ECV-free FCS and 1 μg/ml mERK2 peptide. Splenocytes prepared from B6 mice (2×10$^7$/ml) were cultured in RPMI-1640 medium containing 10% ECV-free FCS, 1 μg/ml TRP-2 (SEQ ID 2: SVYDFFVWL) peptides and 1 μg/ml gp100 (SEQ ID 3: EGSRNQDWL) peptides (Non Patent Literature 21). Splenocytes obtained from BALB/c mice, CMS5a tumor-bearing BALB/c mice, and CD8$^+$ T cell-depleted BALB/c mice (2×10$^7$ cells/ml) were respectively cultured in 12-well plates, which had anti-CD3 monoclonal antibodies (2C11: 2 μg/ml: Biolegend) immobilized thereon, with RPMI-1640 medium containing 10% ECV-free FCS and 1 μg/ml anti-CD28 monoclonal antibody (37.51: eBioscience).

Human peripheral blood monocytes (hPBMC) were prepared by using a Ficoll-Paque® PLUS (manufactured by GE Healthcare) density gradient media and were cultured in 12-well plates, which had OKT3 monoclonal antibodies (2 μg/ml: Biolegend®) immobilized thereon, with RPMI-1640 medium containing 10% ECV-free FCS and 1 μg/ml of CD28 monoclonal antibody (Biolegend®). CD8$^+$ T cell-depleted BALB/c mice were prepared by intravenously injecting a Lyt-2.2-specific monoclonal antibody (400 μg/mouse) so that the number of CD4$^+$ T cells increased in vitro. On day 4 after starting the culture, each medium was changed to RPMI-1640 medium containing 10% ECV-free FCS and a recombinant IL-2 (rIL-2) (100 IU/ml), and further cultured for 3 days. The resulting supernatants were used as ECV sources. The resulting cells were subjected to flow cytometry analyses using a mouse CD4 (GK1.5) specific monoclonal antibody, a CD8 (53-6.7) specific monoclonal antibody, a TCRVβ (H57-597) specific monoclonal antibody, and a V@8.3 (8C1) specific monoclonal antibody, and a human CD4 (OKT4) specific monoclonal antibody, a CD8 (RPA-T8) specific monoclonal antibody, and a TCR (IP26) specific monoclonal antibody (all were obtained from Biolegend), respectively, and to cytotoxicity assays using carboxyfluorescein succinimidyl ester (CFSE).

ECVs were purified according to a protocol that employed ultracentrifugation. Culture supernatant (about 500 ml) was centrifuged at 10,000×g for 40 minutes, filtered through 0.45 μm and 0.22 μm filters, and concentrated to 100 ml by ultrafiltration (Kvick® Lab Packet 50 KD: GE Healthcare). The concentrated supernatant was filtered through a 0.22 μm filter, and ultracentrifuged at 120,000×g for 90 minutes (SW28 rotor: Beckman Courter). The resulting ECV precipitate was suspended in 30 ml of PBS, and washed by ultracentrifugation at 120,000×g. Finally, the ECV precipitate was suspended in 1 ml to 2 ml of PBS, and stored at 4° C.

The protein concentration of the resulting purified ECVs was measured by using a bicinchoninic acid (BCA) protein assay kit (Pierce®). The average number and the average diameter of the purified ECVs were measured by using a nano tracking assay (LM10-HS: Nanosight®). In order to analyze ECV surface proteins by flow cytometry, the ECVs were immobilized on latex beads, and stained with an anti-CD4 monoclonal antibody, an anti-CD8 monoclonal antibody, an anti-CD9 monoclonal antibody (MZ3), an anti-CD63 monoclonal antibody (NVG-2), and ab anti-Vβ8.3 monoclonal antibody, which were conjugated with a fluorescein isothiocyanate (FITC) or phycoerythrin (PE), (all from Biolegend). In 0.1 M 2-morpholino ethanesulfonic acid (MES) buffer, 10 μm polystyrene latex beads were mixed with each ECV sample so that the ECV/latex ratio became 3. Each mixture was shaken on a rotary shaker at room temperature for 2 hours, and then blocked with 400 mM glycine. The resulting latex-bound ECVs were washed 2 times with 2% ECV-free FCS-containing PBS, and stained with monoclonal antibodies.

In order to evaluate the kinetics of the ECVs in vivo and in vitro, 100 μg to 300 μg ECVs were stained with 10 μM SYTO RNASelect Green Fluorescent Cell Stain (Molecular Probes®) at 37° C. for 20 minutes, and unbound staining substances were removed by using a Sephadex® G25 Spin Column.

3. Differentiation Culturing of Bone Marrow Mesenchymal Stem Cells (BM-MSCs)

BM-MSCs were prepared from femurs according to the instructions of the attached document (StemCell Technologies Inc.). Both ends of 10 femurs obtained from BALB/c and CD90.1$^+$ BALB/c, respectively, were cut, and placed in a mortar with 5 ml of 1% BSA-containing PBS. In the mortar, the femurs were softly ground for 5 minutes to be crushed. Red spinal cord cells found were discarded. The red spinal cord cells were removed from crushed femurs 5 times as the 1% BSA-containing PBS was changed to a fresh one, white pieces of the femurs were collected, and incubated with 0.2% Collagenase type I (Sigma)-containing PBS. After the femurs were vigorously shaken in a water bath at 37° C. for 40 minutes, the MSC-containing supernatant was filtered through a 70 μm filter. After washing 3 times, MSCs adhered on a culture plate were cultured in 20% mouse MSC stimulant-containing MesenCult® MSC Basal Medium (StemCell Technologies Inc.) for 30 days. During the culturing, half of the medium was exchanged every 3 days. In order to confirm the ability of the resulting MSCs to differentiate into adipocytes and osteocytes, after 70% confluent MSCs were cultured using the MesenCult® MSC Basal Medium containing 20% adipocyte-forming and osteocyte-forming stimulants for 2 weeks; the cells were respectively stained with Oil Red O (Sigma-Aldrich®) for adipocytes, and Alizarin Red S (Wako® Pure Chemical Industries, Ltd.) and hematoxylin (Muto Pure Chemicals Co., Ltd.) for osteocytes. Early MSC colonies obtained with the MSC stimulant-containing medium were subjected to Giemsa staining (Wako® Pure Chemical Industries, Ltd.). The MSCs were stained with a PE-conjugated anti-CD140a monoclonal antibody and an FITC-conjugated anti-Sca-1 monoclonal antibody, and analyzed by flow cytometry (FACScant II. BD) to confirm the purity of the cultured BM-MSC. The cultured MSCs were further evaluated by flow cytometry for the presence of CD 29, CD 90.1 and CD 105 and for the absence of CD 14, CD 34 and CD 45 by using monoclonal antibodies against each molecule.

4. Preparation of BM-MSC Chimera Mice

Femurs of BALB/c mice (CD90.2) were washed with PBS to prepare bone marrow cells. After culturing, and before transferring of the BM-MSCs, BALB/c mice was irradiated with 6-Gy radiation. Cultured MSCs obtained from CD90.1$^+$ BALB/c mice ($1 \times 10^6$/mouse) were mixed with the bone marrow cells obtained from the femurs of the BALB/c ($5 \times 10^6$/mouse), and the mixed cells were intravenously injected into the irradiated BALB/c mice. The resulting chimera mice were maintained for 2 weeks with 1 mg/ml neomycin (Calbiochem)-containing autoclaved water and X-ray-irradiated feed. On day 60 after the MSC transfer, the CD90.1$^+$ BM-MSC chimera BALB/c mice were used to confirm tumoral MSCs.

5. Processing of CD8$^+$ T Cells and ECVs Released from the CD8$^+$ T Cells In Vivo In order to study the relationship between ECVs released from tumor-invading CD8$^+$ T cells and structural alterations of tumor-associated stroma, CD90.1 DUC18 CD8$^+$ T cells on day 7 of culture ($1 \times 10^7$/mouse) alone or CD90.1 DUC18 CD8$^+$ T cells treated with GW4869 (an ECV-release inhibitor) ($1 \times 10^7$/mouse) were intravenously injected into CMS5a tumor-bearing BALB/c mice and BALB/c nude mice, respectively, on day 10 after subcutaneous inoculation of CMS5a tumor cells (the tumor diameter was about 10 mm). At the same time, an anti-mouse glucocorticoid-induced TNF receptor-related protein (GITR) monoclonal antibody (DTA-1) (2 µg/tumor) was intratumorally injected (inter tumor: i.t.). As explained in Non Patent Literature 18, DTA-1 was used to increase the accumulation of CD8$^+$ T cells in the tumor site. Twenty µg/ml of GW4869 was added 24 hours before termination of the culture. On day 1, day 2, day 3, day 5 and day 7 after injection of the cultured CD90.1 DUC18 CD8$^+$ T cells, CMS5a tumor tissues were collected, and subjected to immunohistochemical staining.

CMS5a cells and B16 cells ($1 \times 10^6$/mouse) were subcutaneously injected into the back skin of each of the BALB/c and B6 mice. In week 2 after the injection, mice having tumor diameters of 1.2-1.5 cm were selected for ECV processing. ECVs obtained from each culture supernatant were intratumorally injected into CMS5a or B16 at a protein amount of 1, 5, or 10 µg, and the tumor diameter after the injection was measured. In addition, on day 3 and day 5 after the ECV injection, the tumors were excised with scissors, and then incubated in 0.5% Trypsin and 1 mM EDTA-containing PBS, at 37° C. for 60 minutes. The resulting tumor cell suspensions were passed through a wool column, washed 3 times with 1% FCS-containing PBS, and subjected to flow cytometry analysis and a test for confirming spheroid formation. For the flow cytometry analysis, an Sca-1, I-Ad, CD11b CD11c, CD73 or CD206 specific FITC-conjugated monoclonal antibody and an F4/80, Gr-1, or CD140a specific PE-conjugated monoclonal antibody were used. With respect to the test for confirming spheroid formation, cells were cultured in 10% FCS-containing RPMI-1640 at a concentration of $1 \times 10^5$/ml.

To the CD90.1$^+$ BM-MSC chimera BALB/c mice in which CMS5a was subcutaneously transplanted, 5 µg ((ECV protein mass)/tumor) of DUC18 ECVs released from CD8$^+$ T cells were intratumorally injected in week 2 after inoculation of the tumor cells. The tumor cell suspensions obtained on day 3 after the ECV injection were stained with an FITC-conjugated CD90.1 specific monoclonal antibody, a PE-conjugated CD140a specific monoclonal antibody, and an allophycocyanin (APC)-conjugated Sca-1 specific monoclonal antibody. After removal of 7-amino actinomycin D (7-ADD)-stained cells, the remaining cells were analyzed by flow cytometry.

B16F10 was subcutaneously inoculated, and 50 µg of DUC18 CD8$^+$ T cell ECVs, CMS5a tumor-bearing BALB/c splenocyte ECVs, and BALB/c splenocyte ECVs, respectively, were intratumorally injected on day 7, day 10, and day 13 after the inoculation. On day 16 after the tumor cell inoculation, tumors derived from B16F10 (having a diameter of about 2 cm) were carefully excised with scissors to observe the tumor invasion. After that, the skin was sutured with a surgical suture. On day 45 after the inoculation of the tumor cells, the presence or absence of lung metastasis of B16F10 was observed.

6. Processing of ECVs Released from CD8$^+$ T Cells In Vitro

ECVs obtained from cultured splenocytes of DUC18, CMS5a tumor-bearing BALB/c, B16 tumor-bearing B6, BALB/c, and B6 were added to culture media of $5 \times 10^4$/ml of CMS5a, B16, CT26, and BM-MSC, respectively. 10% FCS-containing RPMI-1640 medium or BM-MSC medium (20% MSC stimulant-containing MesenCult® MSC Basal Medium) was used for culturing each of the cells. Furthermore, ECVs were added to a mixed culture medium of $5 \times 10^4$/ml of CMS5a, CT26, or B16 cells, and $5 \times 10^4$/ml BM-MSC (cultured in the 10% FCS-containing RPMI-1640 medium), at a concentration of 1 µg or 5 µg (ECV protein)/ml.

On day 4 after starting the culture, the resulting cells were subjected to a test for confirming spheroid formation, and to flow cytometry analyses for confirming the total number of cells and expression of CD140a and/or Sca-1.

7. Fluorescent Immunoassay

Frozen specimens of CMS5a and B16F10 tumors embedded in OCT compound (Sakura® Finetek) were sectioned at a thickness of 3 µm. The tissue sections were air-dried for 2 hours, fixed for 15 minutes in ice-cold acetone, and subjected to immunohistochemistry. The tissue sections were washed 3 times with PBS, and were incubated in a blocking solution (1% BSA, 5% Blocking One Histo (Nacalai Tesque)-containing PBS, and 0.2 µg/ml of an anti-mouse CD16/CD32 monoclonal antibody (Biolegend®)) at 4° C. for 30 minutes. Furthermore, tumor sections on glass slides were double labelled with a PE-conjugated monoclonal antibody and an FITC-conjugated monoclonal antibody dissolved in 1% BSA and 5% Blocking One Histo-containing PBS in a humidified chamber at room temperature for 1 hour. The glass slides were washed 3 times with 0.02% Tween® 20-containing PBS, and treated with DAPI-containing ProLongo Gold Antifade Mountant (Invitrogen-Life Technologies), and observed under a fluorescence microscope (BX53F, manufactured by Olympus®). The pictures of the tissues stained with PE, FITC, and DAPI were superimposed using Photoshop® Elements software (Adobe® Systems). For the fluorescent immunoassay, PE-conjugated monoclonal antibodies against CD8, CD140a, Ki-67, CD31, CD11b, ER-TR7, and TGF-β1, FITC-conjugated monoclonal antibodies against ER-TR7, Sca-1, F4/80, Gr-1, CD90.1, and α-smooth muscle actin (α-SMA) were used.

8. Cytotoxicity Assay

CMS5a cells, CMS7 cells, and CT26 cells were labelled with 2.5 mM carboxyfluorescein diacetate succinimidyl ester (CFSE) at 37° C. for 6 minutes. Cells were washed 3 times with 10% FCS-containing RPMI-1640, and CFSE-labelled CMS5a was used as the target cell. mERK2 peptide-stimulated DUC18 splenocytes were mixed with CFSE-labelled CMS5a cells, CMS7 cells, and B16 cells ($1\times10^5$), respectively, in a 24 well plate at ratios of 1, 5, and 10. After 12 hours of incubation, the remaining cells were analyzed by flow cytometry. For each sample, 20,000 cells not labelled with CFSE were collected, and the number of CFSE-labeled living cells was counted. The survival rate was determined as an average value of 2 wells, and % cellular cytotoxicity was calculated according to the literature (Non Patent Literature 18).

9. Analysis of miRNA in the ECVs

Using a 3D-Gene® Microassay System (Toray® Industries, Inc.), 100 µg of ECVs released from $CD8^+$ T cells, which were obtained from cultured DUC18 (2 lots), CMS5a tumor-bearing BALB/c, and BALB/c splenocytes, and 100 µg of ECVs released from $CD4^+$ T cells, which were obtained from $CD8^+$ T cell-depleted BALB/c mouse splenocytes, were analyzed to identify miRNA. For the normalized raw data of the microarray, each sample was compared. 3 kinds of miRNA were identified as dominant in the ECVs of DUC18, as compared to the ECVs of CMS5a tumor-bearing BALB/c and of $CD4^+$ BALB/c, and were subjected to a functional analysis.

Mouse miR298-5p (SEQ ID 4: GGC AGA GGA GGG CUG UUC UUC CC), miR-298-3p (SEQ ID 5: GAG GAA CUA GCC UUC UCU CAG C), miR1943-5p (SEQ ID 6: AAG GGA GGA UCU GGG CAC CUG GA), miR-1943-3p (SEQ ID 7: CAG GUG CCA GCU CCU CCC UUC), miR-5099-$5_p$ (SEQ ID 8: GUU AGA AAU UAC AUU GAU UUA A), miR5099-3p (SEQ ID 9: UUA GAU CGA UGU GGU GCU CC), miR-150-5p (SEQ ID 10: UCU CCC AAC CCU UGU ACC AGU G), miR-150-3p (SEQ ID 11: CUG GUA CAG GCC UGG GGG AUA G), miR-223-5p (SEQ ID 12: CGU GUA UUU GAC AAG CUG AGU UG), miR-223-3p (SEQ ID 13: UGU CAG UUU GUC AAA UAC CCC A), miR-3470b-$5_p$ (SEQ ID 14: UCA CUC UGU AGA CCA GGC UGG), and miR-3470b-3p (SEQ ID 15: CCU GCC UCU GCC UCC CGA) were synthesized according to RNA sequences in the miRBase, and annealed between 5p and 3p (Hokkaido System Science Co., Ltd.).

ECVs obtained from human PBMC were used as temporary vesicles for the functional analysis of synthesized miRNA. In a 12 well plate, anti-CD3 monoclonal antibody and anti-CD28 monoclonal antibody were added to RPMI-1640 medium containing 10% FCS and 100 IU/ml rIL-2, and the human PBMCs were cultured therein and stimulated for 3 days. The cells were washed 2 times with RPMI-1640 medium not containing FCS, and the stimulated human PBMCs ($1\times10^8$) were suspended in 1.5 ml of 1% DMSO-containing RPMI-1640 medium. After mixing the suspension with an RNA pool of miR-298 (50 µg), miR-1943 (50 µg), and miR-5099 (50 µg), or of miR-150 (50 µg), miR-223 (50 µg), and miR-3470b (50 µg), the mixture was subjected to electroporation. The resulting cells were cultured in 10% FCS-containing RPMI-1640 medium not containing ECV for 20 hours. After the supernatants were filtered through 0.45 and 0.22 filters, they were ultracentrifuged (120,000 g) to obtain ECVs that contained synthesized miRNA.

10. Investigation of MSC Cytotoxic miRNA

Monocytes (PBMCs) were separated from human peripheral blood by using Ficoll®. The PBMCs ($2\times10^5$ cells/ml) were cultured in GT-T503 medium (TAKARA Bio Inc.) supplemented with 0.6% autologous plasma, 0.2% human serum albumin (CSL Behring), and 600 IU/ml rIL-2, for 2 weeks. Culture plates coated with 5 µg/ml OKT3 antibody (BioLegend®) and 25 µg/ml RetroNectin® (TAKARA Bio Inc.) were used. The cell populations after culturing were analyzed for the presence or absence of CD4 and CD8 by flow cytometry. Furthermore, culture supernatants after culturing were centrifuged at 10,000 g for 20 min, and filtered through 0.45 µm and 0.22 µm filters to remove cell debris and aggregated proteins. In addition, the filtrate was ultra-centrifuged at 120,000 g for 70 min to separate exosomes released from cultured human T cells.

The diameters of the resulting exosomes were measured by Nano-Tracking Analysis (NTA). Furthermore, flow cytometry analyses (BD: FACSCant) were conducted by using a variety of antibodies electrostatically bound to latex beads (4 µm diameter: Life Technologies) to investigate surface molecules on the T cells and exosomes.

miRNA contained in exosomes released from cultured human T cells was analyzed by microarray (Toray: 3D-Gene®). The above-identified 40 kinds of miRNA were synthesized in descending order of abundance. The synthesized miRNA were added to cultured mesenchymal stem cells (MSCs) derived from human adipose tissues, and cellular cytotoxicity was investigated. Cellular cytotoxicity was investigated by the following methods: (1) a method in which synthesized miRNA is added to cultured MSCs, and then the cultured MSCs are subjected to Giemsa staining (Wako®), and (2) a method in which a variety of miRNA is added to MSCs cultured on a dedicated plate, and then the cell survival of the MSCs is measured by using an xCEL-Ligence® (ACEA BioSciences) instrument, which measures cell survival using electrical resistance values.

11. Statistical Analysis

Data of 2 groups were analyzed by using the Mann-Whitney U test. Equality of variance was confirmed by the Levene's test, and comparison of data between 2 groups was analyzed by the Student's t-test. Statistical significance was determined with $p<0.05$. SPSS® statistical software v21.0 (IBM) was used for the statistical calculations.

Test Results

1. Suppression of Tumor Proliferation by ECVs Released from $CD8^+$ T Cells

First, we examined the influence of ECVs derived from TCR-stimulated lymphocytes on tumor proliferation. Splenocytes of the TCR gene transgenic DUC18 mice, which were stimulated with mutated ERK2 peptide, and splenocytes of the CMS5a tumor-bearing BALB/c mice, of the BALB/c mice, and of the $CD8^+$ T cell deficient BALB/c mice, and hPBMC, which were stimulated with both a CD3 specific monoclonal antibody and a CD28 specific monoclonal antibody, were cultured for 4 days, and then further cultured for 3 days in the presence of rIL-2 (100 IU/ml). All of the splenocytes of the cultured DUC18, CMS5a tumor-bearing BALB/c, and BALB/c exhibited the phenotype of $CD4^-$ $CD8^+$ on day 4 of the culture. With regard to the splenocytes of $CD8^+$ T cell deficient BALB/c mice, 65% were $CD4^+$ and $CD8^-$. With regard to the cultured hPBMC, CD8 was exhibited 70% and CD4 was exhibited 30%, respectively (FIG. 1A).

Figure 2:
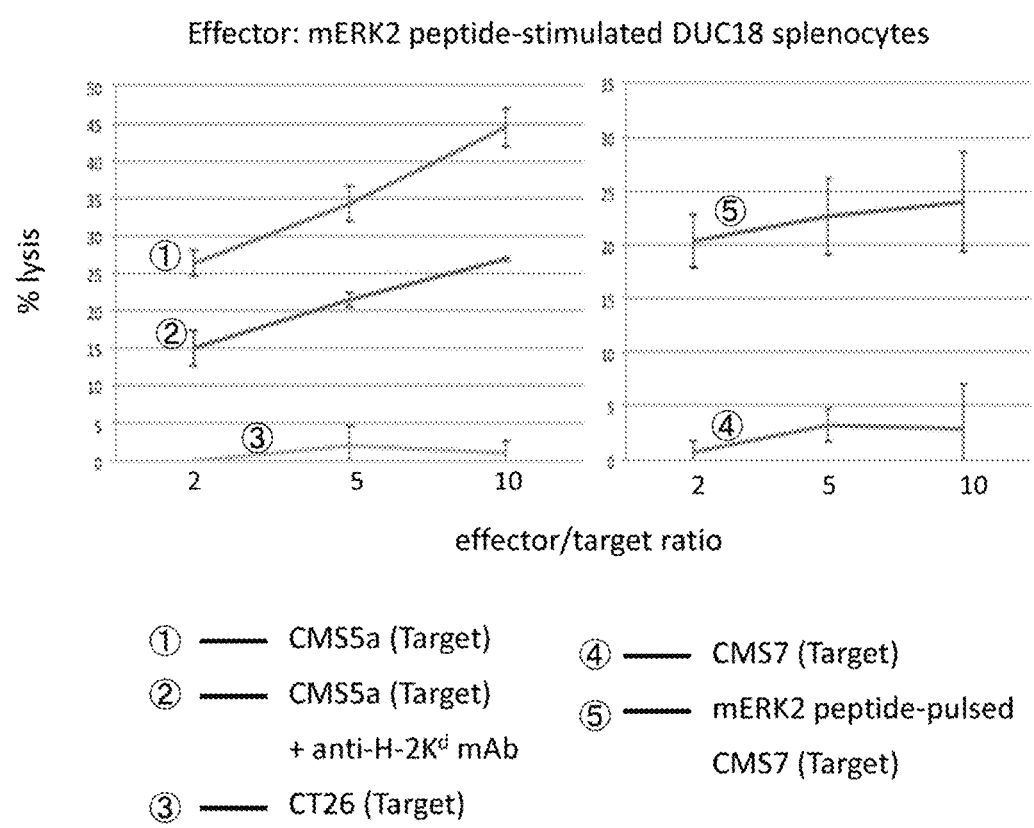
FIG. 2 shows two graphs that depict the lytic activities of DUC18 CD8$^+$ T cells specific against the corresponding tumors. Cytotoxicity assays were conducted for DUC18 CD8$^+$ T cells stimulated with mutated ERK2 peptide, by using CMS5a, H-2Kd-neutralizing CMS5a, CT26, CMS7, and mERK2 peptide-pulsed CMS7, respectively, as the target cells.
Figure 3:
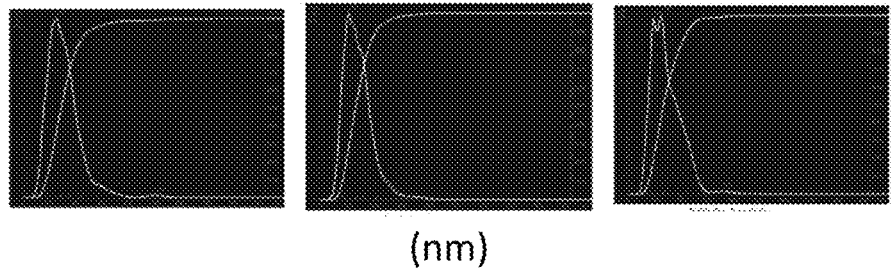
FIGS. 3A and 3B show the total protein concentrations and the total numbers and average diameters of ECV particles used in this study. More specifically.
Figure 3:
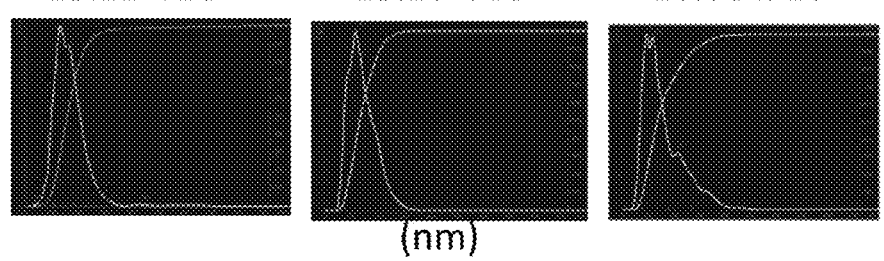
Figure 3:
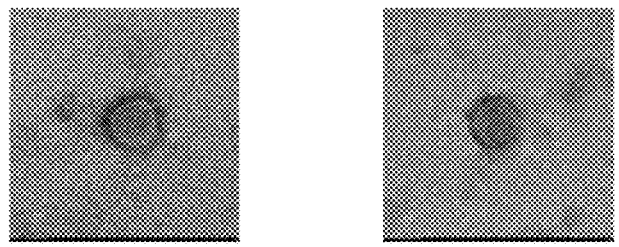

Furthermore, the cultured $CD8^+$ DUC18 splenocytes exhibited cytotoxicity against $mERK2^+$ CMS5a, but did not exhibit toxicity against $mERK2^-$ CMS7 or CT26; mERK2 peptide-stimulated CMS7 were lysed (FIG. 2). The obtained supernatants were ultracentrifuged, and ECVs were purified from each of the cells (DUC18, CMS5aTB, BALB/c, CD4 BALB/c, and hPBMC). All types of ECVs were present in the supernatants at protein concentrations of 0.6 μg/ml to 1.0 μg/ml, at about $4 \times 10^9$ to $8 \times 10^9$/ml, with average diameters of 110 nm to 140 nm (FIGS. 3A and 3B). Surface markers of the DUC18 ECVs were investigated. In accordance with the phenotypes of the parental cells, the DUC18 ECVs expressed CD8, TCRVβ8.3, and CD63 at low levels, and highly expressed CD9, which was previously known as an ECV marker (FIG. 1B).

Figure 4:
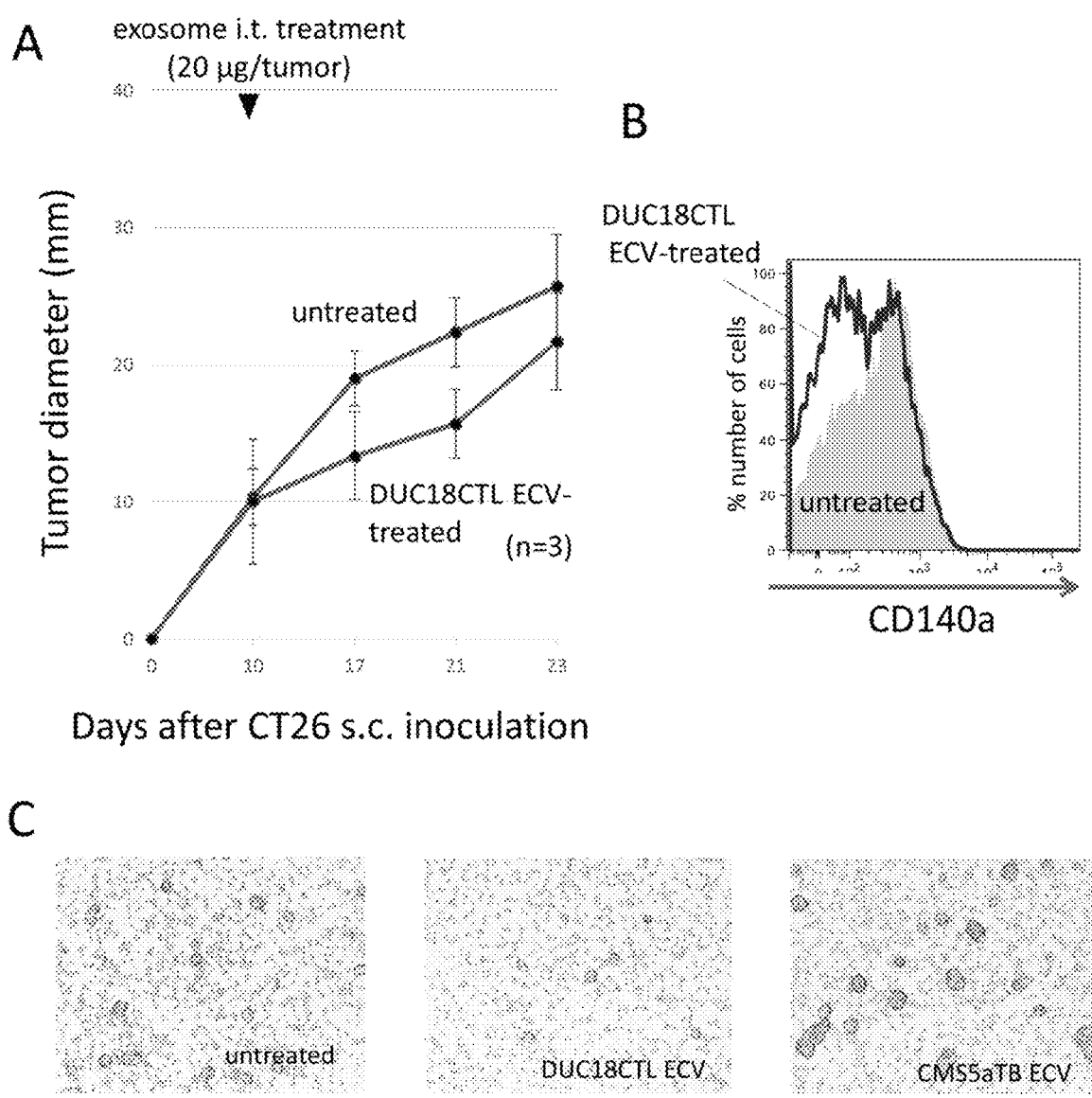
FIGS. 4A-4C concern the downregulation of CT26 tumor proliferation by DUC18 ECV administration. More specifically.

To the BABL/c mice in which CMS5a was subcutaneously inoculated, DUC18 ECVs, CMS5aTB ECVs, and BALB/c ECVs were intratumorally (having a tumor diameter of 1.2 cm to 1.5 cm) injected. Surprisingly, proliferation of CMS5a treated with DUC18 ECVs was terminated and proliferation of CMS5a treated with BALB/c ECVs significantly decreased, as compared to CMS5aTB ECV-treated or untreated groups (FIG. 1C). Moreover, spheroid formation after 1 day culture of CMS5a suspensions was not observed in the DUC18 ECV-treated group, but was observed in the untreated group and in the CMS5a TB ECV-treated group (FIGS. 1C and 1D). Similarly, in the CMS5a tumor-bearing group and the CT26 tumor-bearing group of the BALB/c nude mice, intratumoral injection of DUC18 ECVs decreased the tumors. In addition, when CD4 BALB/c ECVs were intratumorally injected into CMS5a tumors, suppression of proliferation was not observed (FIGS. 1C and 4). In the CMS5a tumors into which DUC18 ECV and BALB/c ECV were injected, a decrease in Ki-67 expression was observed immunohistochemically (FIG. 1E). When these findings are taken together, it is understood that, when not in a tumor environment, activated CD8$^+$ T cells release ECVs that suppress tumor proliferation in a cellular immunity independent and non-specific manner.

Figure 5:
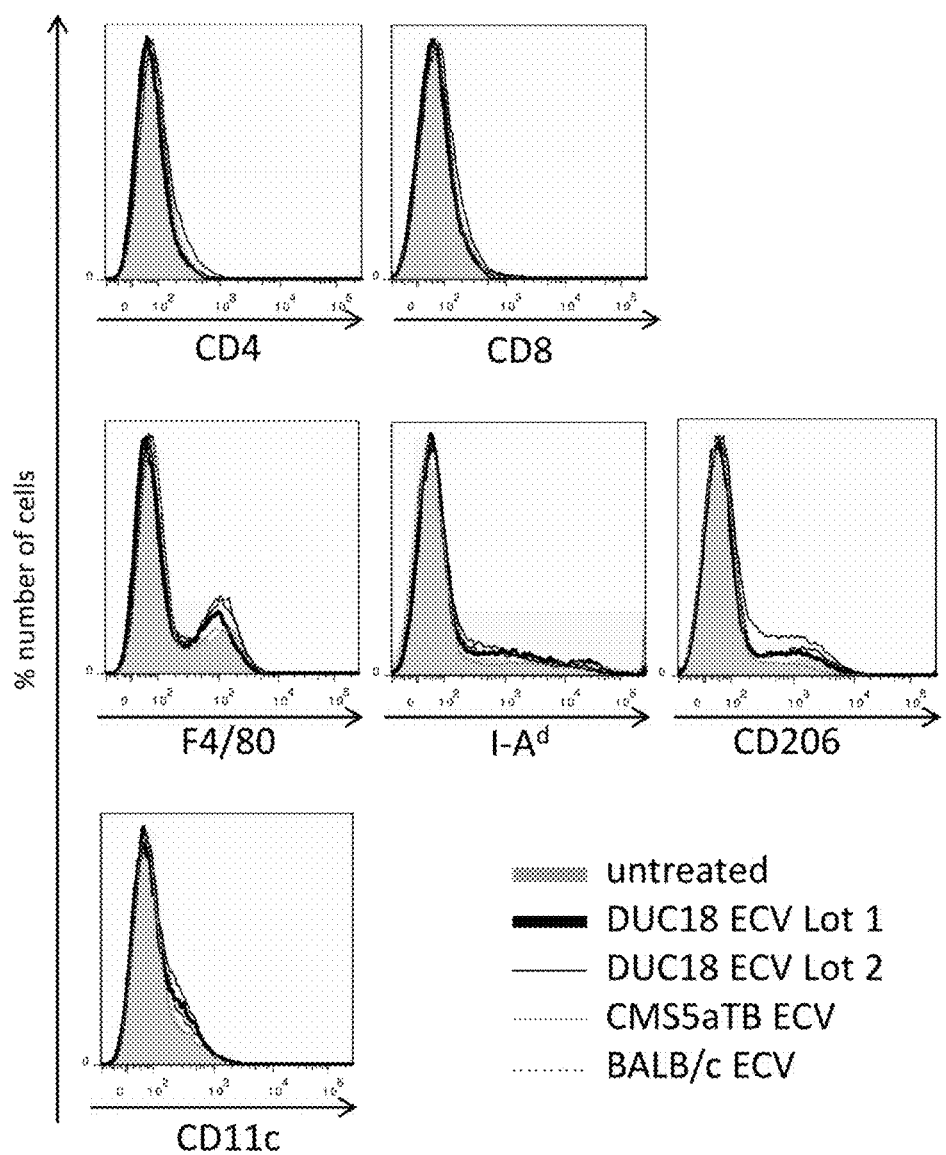
FIG. 5 shows six graphs concerning ECVs derived from $CD8^+$ T cells that do not regulate the abundance of tumor T lymphocytes, macrophages, and dendritic cells. More specifically, DUC18 ECVs (Lots 1 and 2), CMS5a TB ECVs and BALB/c ECVs, respectively, were intratumorally injected into CMS5a-inoculated BALB/c mice. On day 3 after administration, tumor suspensions were stained with monoclonal antibodies against CD4, CD8, F4/80, I-Ad, CD206, and CD11c, respectively, and analyzed by flow cytometry.
Figure 6:
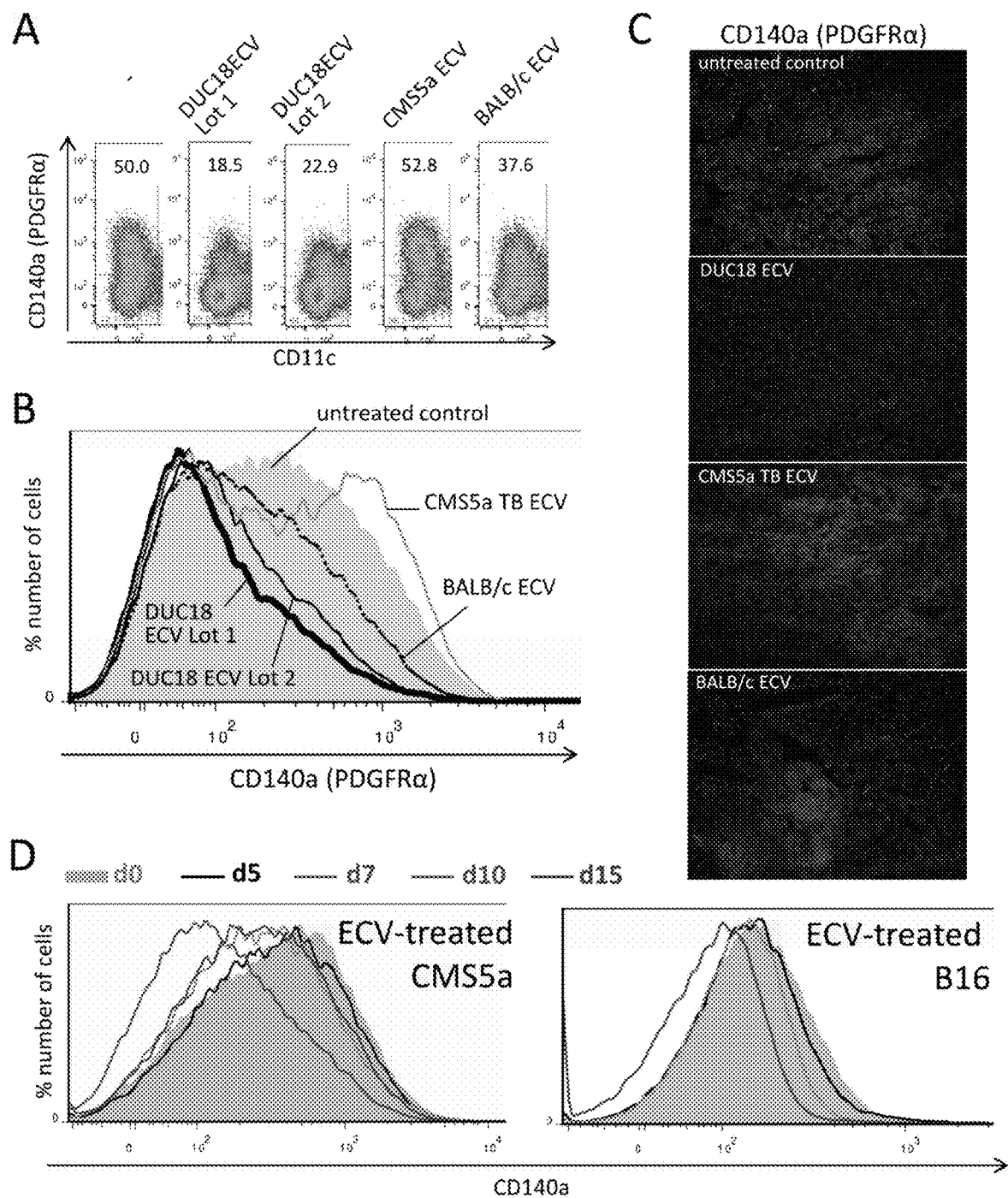
FIGS. 6A-6D concern the downregulation of CD140a (PDGFRα) expression induced by intratumoral injections of ECVs released from $CD8^+$ T cells. More specifically, FIGS. 6A and 6B respectively show a dot plot and a histogram concerning two lots of DUC18 ECVs that were intratumorally injected into CMS5a tumors. CD140a expression was analyzed by flow cytometry, and the results were compared with a CMS5a ECV-treated group and a BALB/c ECV-treated group.
Figure 7:
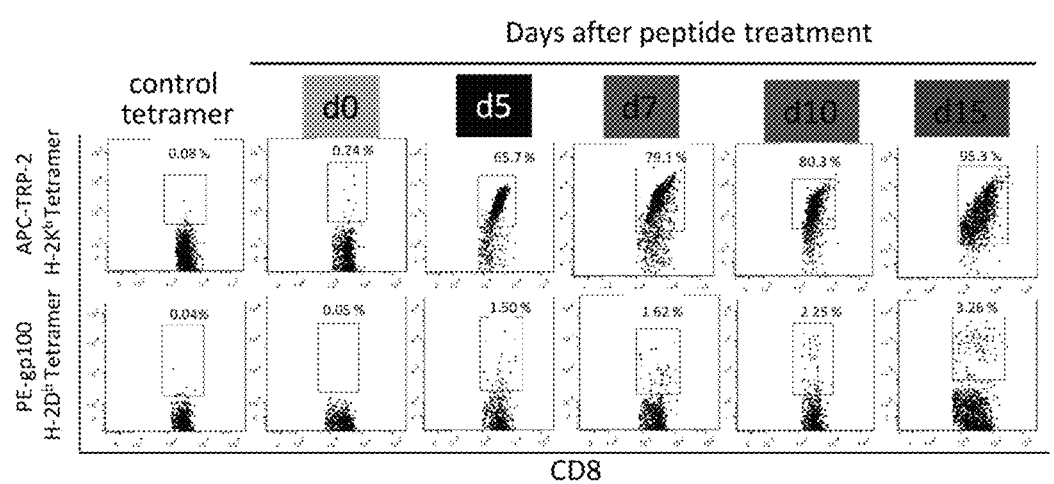
FIG. 7 shows the results of the examination of the kinetics of B6 splenocytes stimulated with TRP-2 and gp100 peptides. More specifically, B6 splenocytes were stimulated with TRP-2 and gp100 peptides; on day 0, day 5, day 7, day 10, and day 15 after stimulation, induction of TRP-2 or gp100 specific $CD8^+$ T cells was confirmed by flow cytometry using the corresponding tetramers, as shown in the graphs of FIG. 7. An unrelated tetramer was used as a control.

2. Decrease in CD140a Expression in Tumors by ECVs Released from CD8$^+$ T Cells It was conjectured that activated ECVs released from CD8$^+$ T cells either directly suppress an increase in tumor cells, or suppress tumor proliferation by acting against tumor-bearing cells. In order to answer this question, we investigated the change of tumor invading cell populations that have been known to regulate tumor proliferation. On day 3 after the injection of DUC18 ECVs or BABL/c ECVs into CMS5a tumors, in both cases there were no changes in the proportion of F4/80$^+$ CD206$^+$ macrophages or F4/80$^+$ I-A$^{d+}$ macrophages, in the proportion of CD11c$^+$ dendritic cells and CD11b$^+$ Gr-1$^+$ MDSC or in the proportion of CD4$^+$ and CD8$^+$ lymphocytes (FIG. 5); however, the number of proliferating tumor cells and the number of CD140$^+$ mesenchymal marker positive cells, which include BM-MSCs and CAF cells, were greatly decreased by the administration of the DUC18 ECVs (FIGS. 6A and 6B). These data were confirmed also by the fact that expression of CD140a was decreased in CMS5a into which DUC18 ECVs and BALB/c ECVs were injected (FIG. 6C). Alternatively, the kinetics of ECV expression were confirmed by ECVs obtained from culture supernatants of TRP-2 and GP100 peptide-stimulated B6 splenocytes on day 5, day 7, day 10, and day 15. TRP-2 specific CD8$^+$ lymphocytes and gp100 specific CD8$^+$ lymphocytes gradually increased in the culture, and they reached 95% and 3% respectively on day 15 (FIG. 7). Interestingly, the peak of decrease in CD140a expression by intratumoral injection was observed in ECVs obtained on day 7 of the culture, and ECVs released from TRP-2 and gd100 specific CD8$^+$ T cells act similarly against unrelated CMS5a and related B16 (FIG. 6D). A decrease in functional ECV production by peptide specific CD8$^+$ T cells observed on day 15 after injection was thought to be related to the decline of lymphocytes.

These results demonstrate that ECVs released from CD8$^+$ T cells affect proliferation and progression of tumors in a non-specific manner.

Figure 8A:
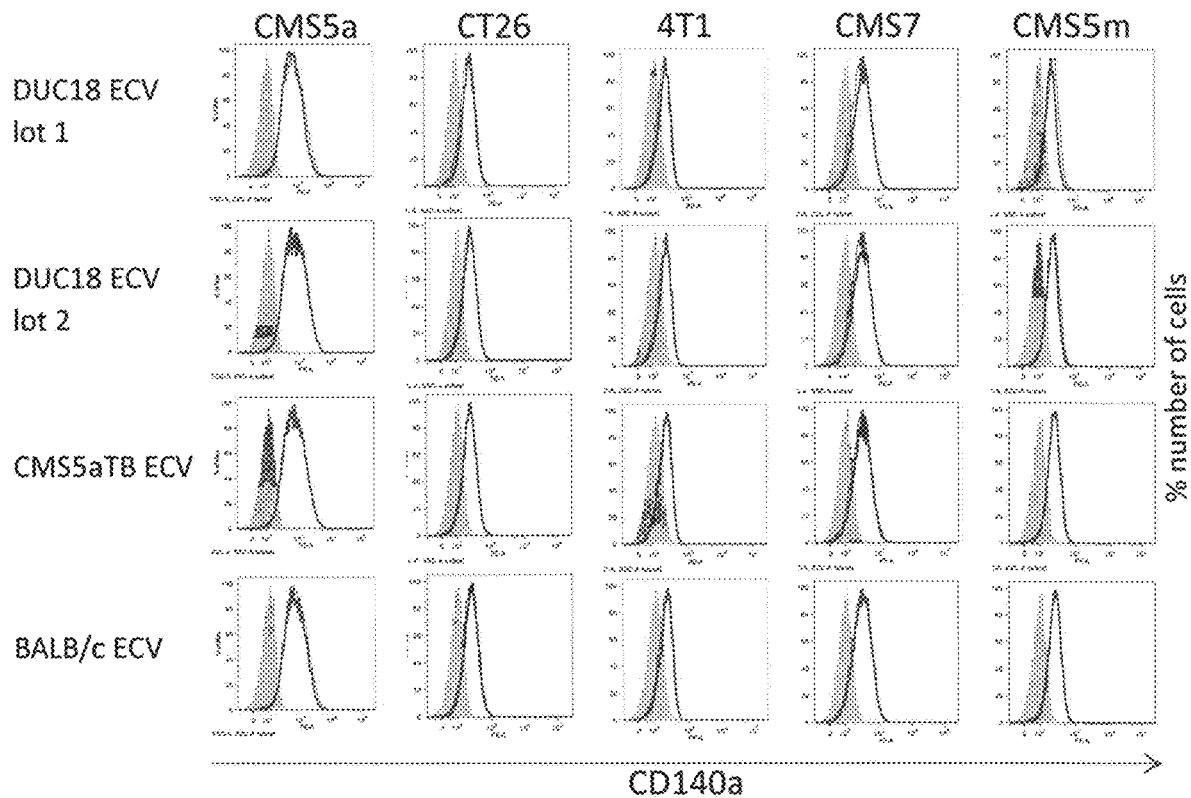
FIGS. 8A and 8B concern ECVs derived from $CD8^+$ T cells that do not directly suppress CD140a expression or apoptosis of cultured tumor cells. More specifically.
Figure 8B:
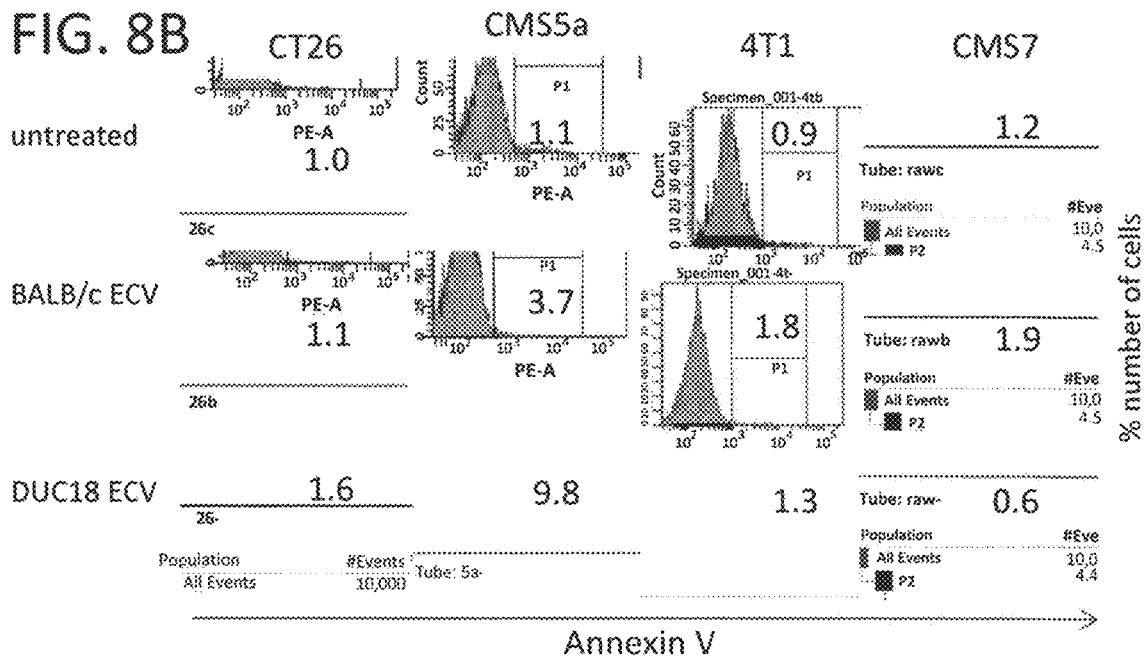
Figure 9:
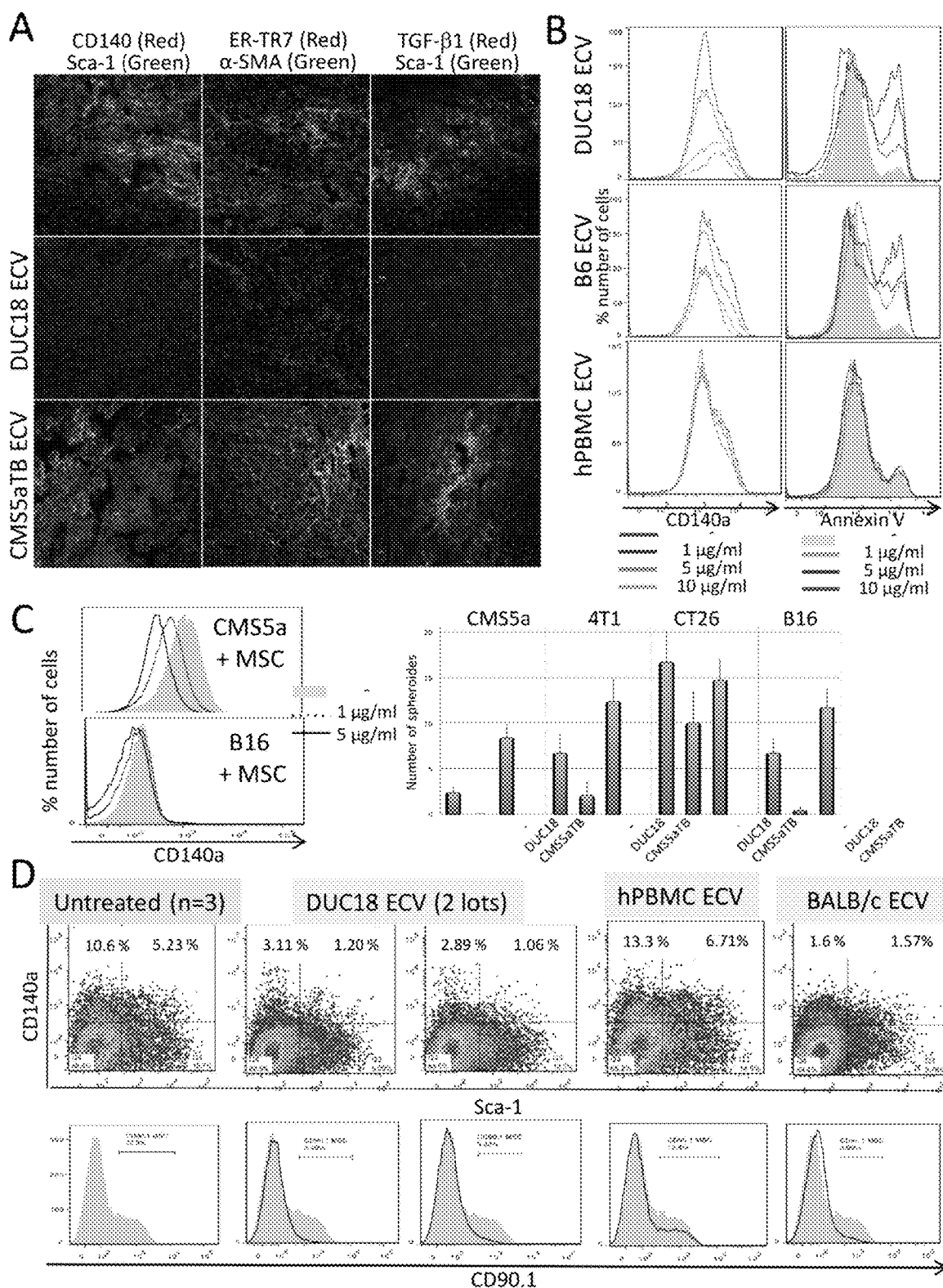
FIGS. 9A-9D concern the fact that BM-MSC undergo apoptosis owing to ECVs released from $CD8^+$ T cells, whereby BM-MSC mediated tumor proliferation is suppressed.
Figure 10:
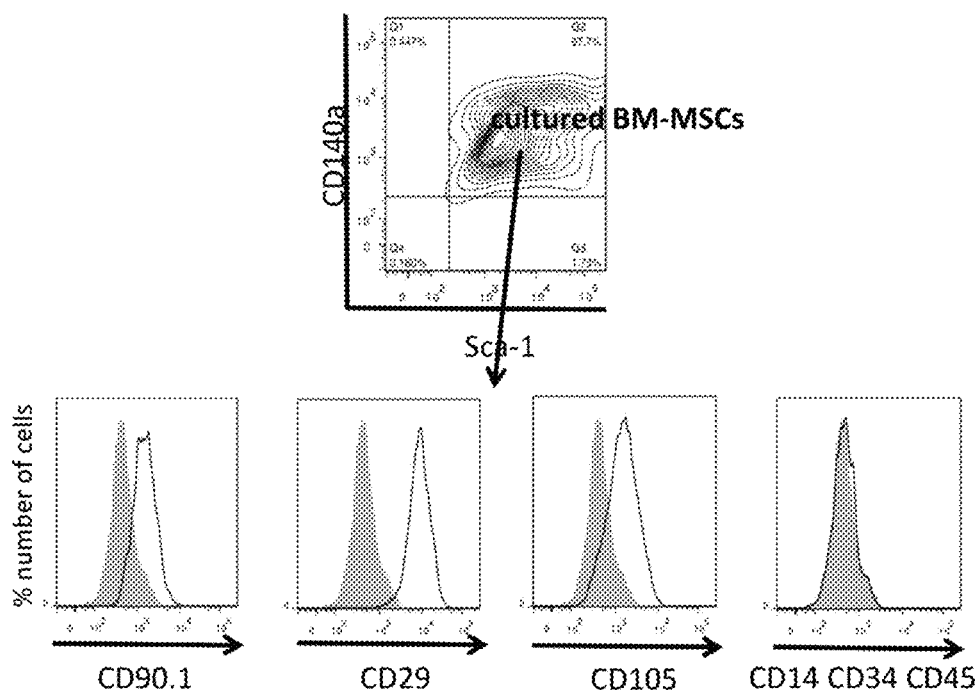
FIGS. 10A-10C concern the characterization of cultured CD90.1 BM-MSC. More specifically, FIG. 10A graphically shows the results of a flow cytometry analysis that was performed as follows: The CD90.1 BM-MSC were cultured for 2 months and then were stained with a mixture of a PE-conjugated CD140a monoclonal antibody, an APC-conjugated Sca-1 monoclonal antibody, an FITC-conjugated CD90.1, CD29, or CD105 monoclonal antibody, or CD14, CD34, and CD45 monoclonal antibodies and the resulting cells were analyzed by flow cytometry.
Figure 10:
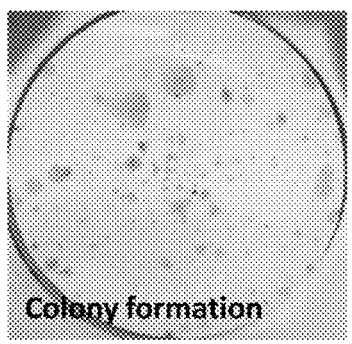
Figure 10:
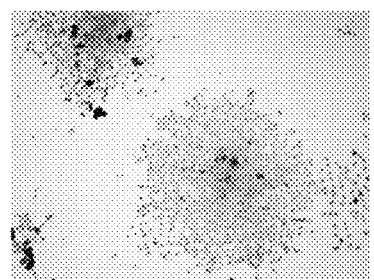
Figure 10:
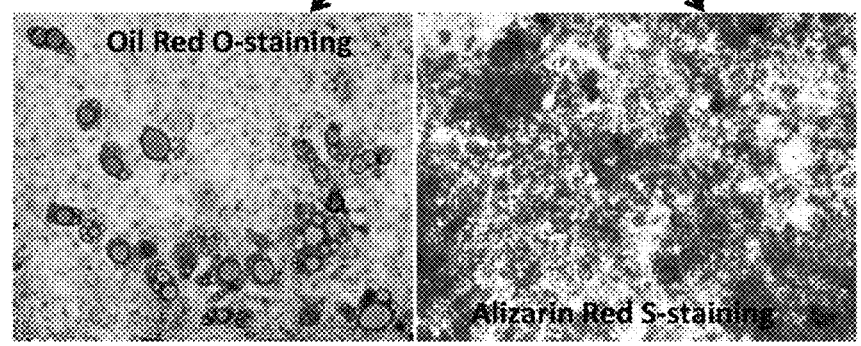
Figure 11:
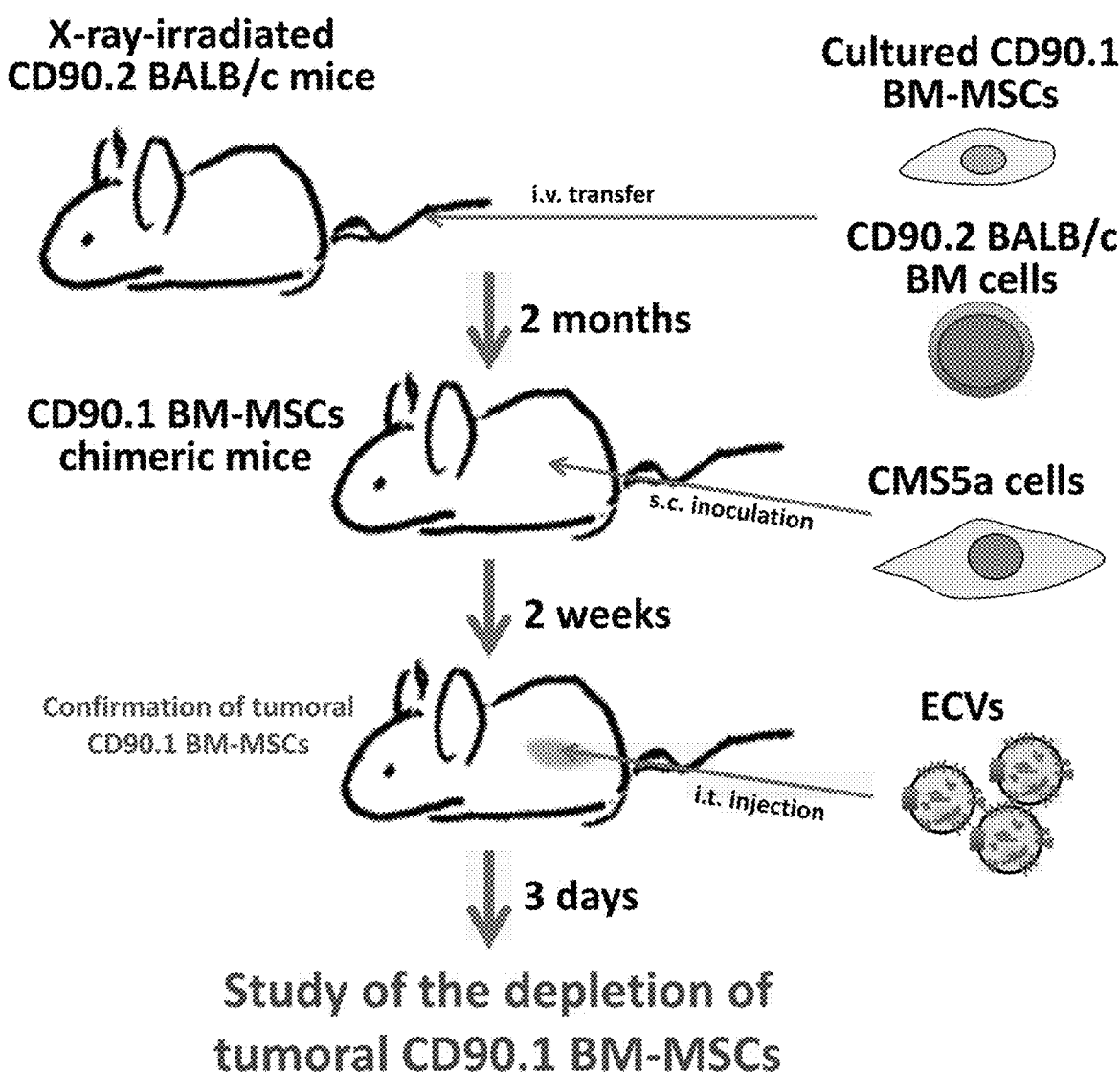
FIG. 11 is a schematic diagram of the strategy for preparing CD90.1 BM-MSC chimera BALB/c mice that were used to clarify the role of ECVs released from $CD8^+$ T cells in the apoptosis of tumor-invading MSC. Cultured CD90.1 BM-MSC and BALB/c BM cells were intravenously transferred into BALB/c mice, which had been previously irradiated with 6 Gy radiation. In month 2 after the cell transfer, CMS5a tumor cells were subcutaneously inoculated into the CD90.1 BM-MSC chimera mice. In week 2 after the CMS5a inoculation, DUC18 ECVs, BALB/c ECVs, and hPBMC ECVs were injected into the CMS5a tumors (having a diameter of about 1 cm). On day 3 after the ECV injection, the resulting splenocytes were collected, and depletion of tumoral CD90.1$^+$ cells was analyzed by flow cytometry.

3. Mesenchymal Stromal Cell-Mediated Downregulation of Malignant Transformation of Tumors by ECVs Released from CD8$^+$ T Cells DUC18 ECVs do not directly affect CD140a expression levels not only in CMS5a cells, but also in CD26, 4T1, and B16 cells. In vitro annexin V staining demonstrated that apoptosis cannot be induced in CMS5a, CT26, 4T1, or CMS7, and thus direct suppression effects of ECVs released from CD8$^+$ T cells against tumor cells was negated (FIG. 8). Moreover, in immunohistochemistry, a CMS5a tumor treated with DUC18 ECVs exhibited depletion of BM-MSC (CD140a$^+$ Sca-1$^+$) and depletion of CAF (ER-TR7$^+$ α$^-$ smooth muscle actin [SMA]$^+$), and a decrease in TGF-β1 expression (FIG. 9A). Therefore, we investigated the relationship between BM-MSCs, which are representative of mesenchymal tumor-associated stromal cells, and ECVs released from CD8$^+$ T cells. The number of cultured BM-MCSs dramatically decreased upon the addition of DUC18 ECVs and B6 ECVs on day 3 after the addition (FIG. 10); however, such a reaction was also observed in ECVs released from human PBMC (FIG. 9B). In addition, when DUC18 ECVs were added to a mixture of cultured BM-MSCs and tumor cells, CD140a expression of CMS5a and B16 cells and spheroid formation of CMS5a, 4T1, CT26, and B16 were downregulated in the presence of DUC18 ECV as compared to the CMS5aTB ECV-treated group (FIG. 9C). Accordingly, transition of tumor to mesenchyme induced by interaction with BM-MSCs was thought to be inhibited due to the loss of BM-MSCs caused by ECVs released from CD8$^+$ T cells. In order to confirm that tumor invading BM-MSCs are depleted in vivo in the presence of ECVs derived from CD8$^+$ T cells, DUC18 ECVs, BALB/c ECVs and hPBMC ECVs were intratumorally injected into CMS5a tumor-bearing CD90.1$^+$ BM-MCS chimera BALB/c mice (FIG. 11).

CD90.1$^+$ cells containing BM-MSC differentiated cells (for example, CAF, cancer-related fibroblasts, pericytes), which were 5% and about 15% of the injected CD140a$^+$ Sca-1$^+$ BM-MSC, were found inside the CMS5a tumors of the chimera mice. These tumor invading CD90.1$^+$ cells were not affected by hPBMC ECVs, while they were depleted by intratumoral injection of DUC18 ECVs and BALB/c ECVs (FIG. 9D).

Figure 12:
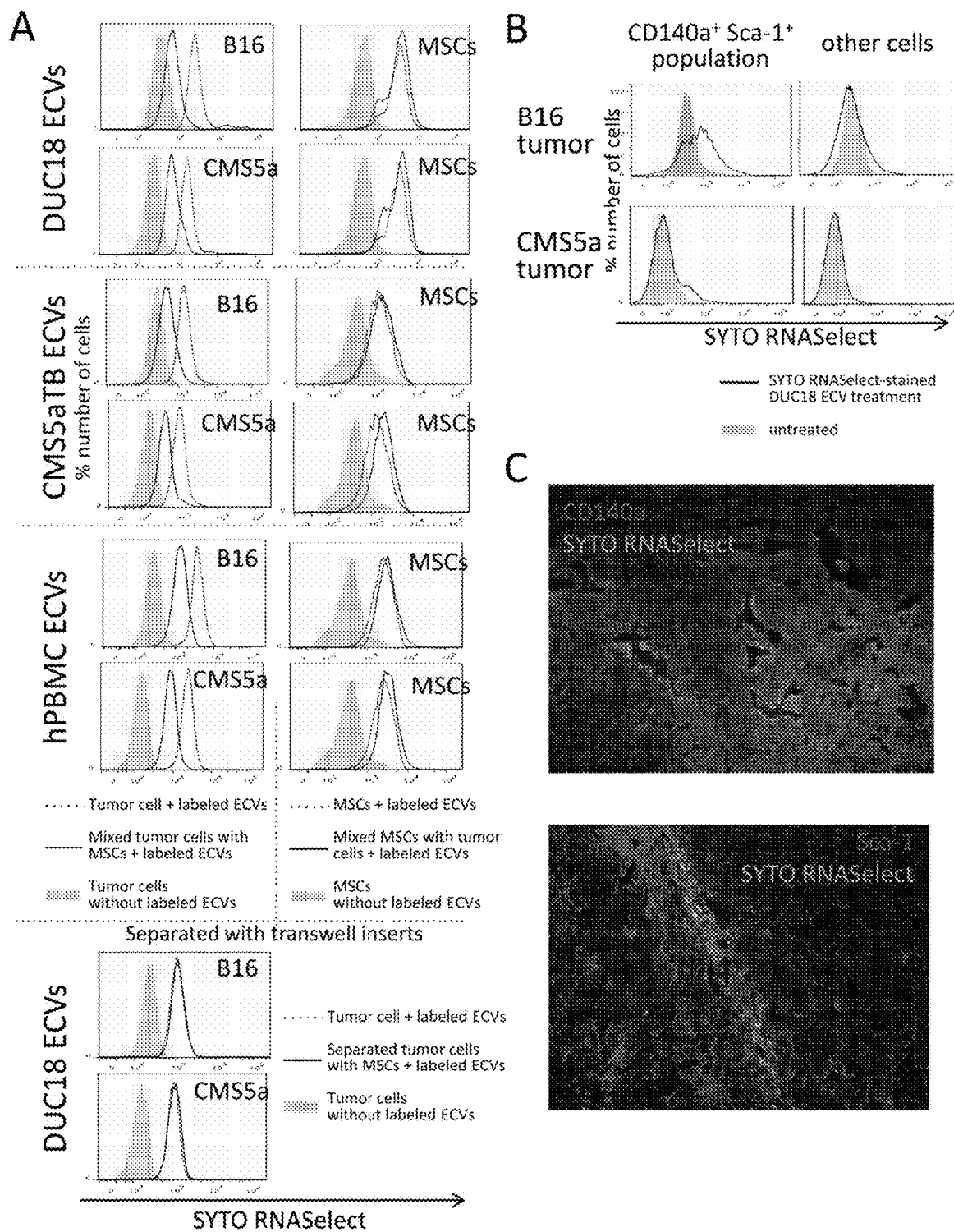
FIGS. 12A-12C concern ECV-derived RNA being functionally taken up into BM-MSCs, but not into tumor cells. More specifically, FIG. 12A graphically shows the results of a flow cytometry analysis that was performed as follows: B16 cells or CMS5a cells and BM-MSC were co-cultured or individually cultured for 3 days, and then SYTO RNASelect-stained DUC18, CMS5a TB or hPBMC ECV was added thereto. The intensities of green fluorescence emitted from SYTO RNASelect in B16, CMS5a, or BM-MSC were analyzed by flow cytometry 2 hours after the ECVs were added, as illustrated in the graphs. Untreated tumor cells and BM-MSC were used as negative controls. B16, CMS5a, and BM-MSC, respectively, treated with SYTO RNASelect-stained ECVs were individually used as positive controls.
Figure 13:
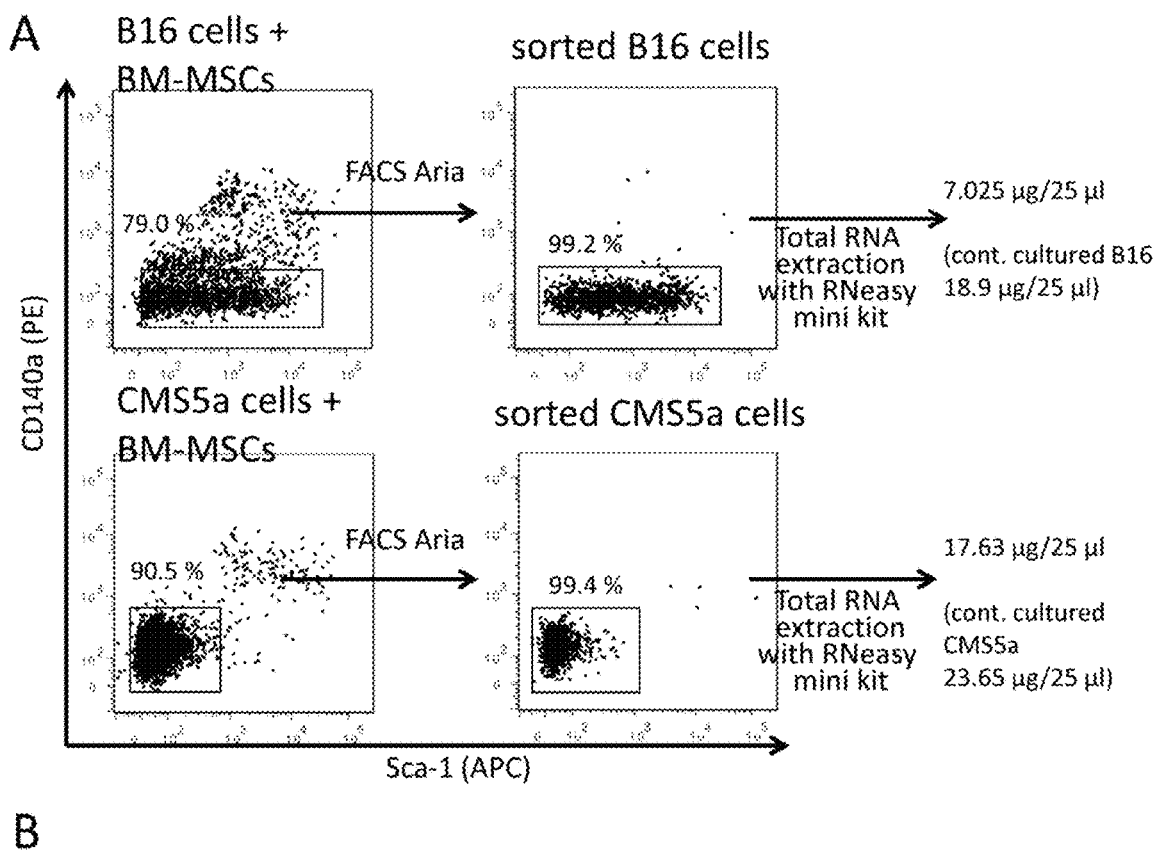
FIGS. 13A and 13B depict the results of total mRNA microarray analyses of tumor cells contacted with cultured BM-MSC. More specifically, FIG. 13A graphically shows the result of the total mRNA microarray analysis that was performed in the following manner: B16 cells or CMS5a cells were cultured individually or co-cultured with cultured BM-MSC for 3 days. Tumor cells were separated from BM-MSC by using a fluorescence-activated cell sorter. Total RNA was extracted from tumor cells co-cultured with BM-MSC or tumor cells cultured alone, and subjected to total mRNA microarray analysis using an RNeasy® mini kit as illustrated in the graphs.

ECVs are taken up into both BM-MSC and tumor cells. B16 cells and CMS5a cells co-cultured with BM-MSC take up SYTO RNASelect-labelled DUC18, CMS5a TB, or hPBMC ECVs, and the intensities of green fluorescence decreased soon after the uptake. Tumor cells in contact with BM-MSCs seem to decompose ECV-derived miRNA immediately after they uptake ECVs (FIG. 12A). According to RNA microarray analysis (3D-Gene®, manufactured by Toray®), it was demonstrated that lysozyme mRNA greatly increased in tumor cells contacted with BM-MSC (FIG. 13B). Flow cytometry analysis and immunohistochemistry analysis of CMS5a treated with SYTO RNASelect-labelled DUC18 ECVs also demonstrated that the green fluorescence label was observed within the region of CD140a$^+$ or Sca-1$^+$ stroma 30 minutes after the ECV treatment, but was not observed within the region of cancerous tissue (FIGS. 12B and 12C).

Figure 14A:
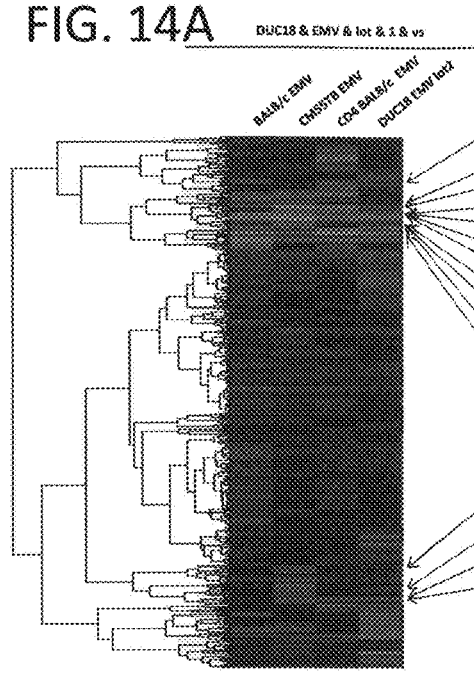
FIGS. 14A-14C concern the involvement of miRNA in the depletion of cultured BM-MSC. More specifically.
Figure 14B:
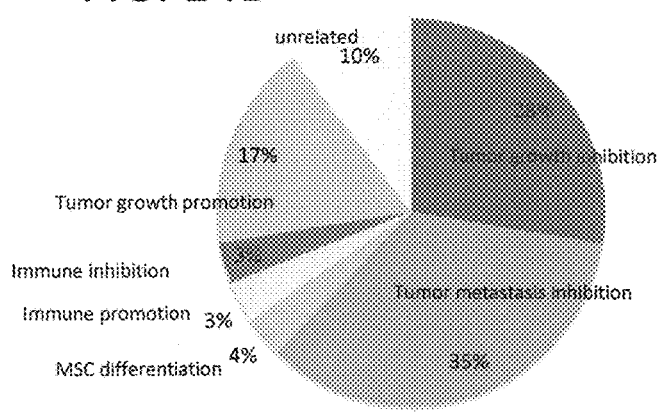
Figure 14C:
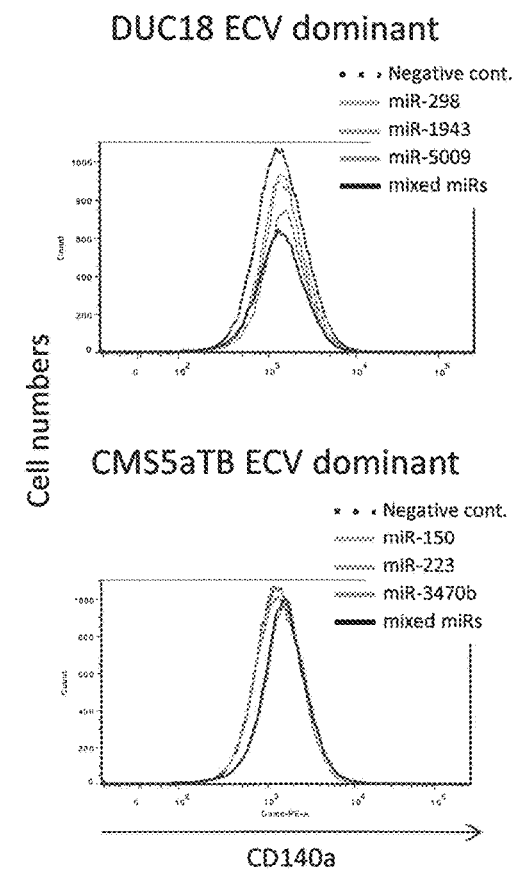

4. Involvement of Novel miRNA in the Inhibition of Tumor Progression Mediated by Mesenchymal Stromal Cells Because hPMBC ECVs are unresponsive, but self- and allogenic CD8$^+$ T cells-derived ECVs are responsive, with respect to the killing of BM-MSCs, involvement of miRNA contained in the ECVs was suggested. Therefore, total RNA derived from DUC18 (2 lots) ECVs, CMS5a TB ECVs, and CD4 Balb/c ECVs were analyzed by miRNA microarray (3D-Gene®, manufactured by Toray®). By comparing global normalization values and heat mapping data among the miRNA, it was clarified that miR-298, miR-351, miR-700, miR-141, miR-1943, miR-1249, miR-344g, miR-23b, miR-370, miR-1199, miR-5113, miR-5114, miR-6347, miR-6392, and miR-5099 were dominant in DUC18 ECVs, and that miR-150, miR-223, and miR-3470b were dominant in CMS5a ECVs (FIG. 14A). As expected, since self-suppressive effects of tumors have been reported for DUC18 ECV-derived miR-298, miR-141, miR-1249, miR-23b, and miR-370, the above-identified kinds of miRNA were confirmed to be correct (FIG. 14B and FIG. 15). Furthermore, 5p and 3p oligonucleotides of 3 kinds of miRNA, which were predicted to be the most effective among the DUC18 ECVs, were synthesized, annealed, and introduced into cultured BM-MSCs. As compared to cases in which miR-1943 and miR-5099 were introduced, introduction of miR-298 induced a large decrease in BM-MSCs (FIG. 14C). When miR-150, miR-223, and miR-3470b, which were dominant in CMD5a TB ECVs, were introduced, the killing action against BM-MSCs was not observed. From these results, miR-298 was found for the first time to be a miRNA capable of killing BM-MSCs. Considering the similarity of immune systems and from basic research of cancer, specific miRNA having such a function are present even in miRNA contained in exosomes obtained from human cytotoxic T cells.

5. Prevention of Invasion and Metastasis of Tumors by Treating with ECVs Released from CD8$^+$ T Cells Invasion and metastasis of tumors are indicators of epithelial to mesenchymal transition and aggravation of tumors. Therefore, in order to investigate the effects against invasion and metastasis, we intratumorally injected DUC18 ECVs, CMS5a TB ECVs, and BALB/c ECVs into mice, in which B16F10 cells had been previously subcutaneously inoculated, on day 10, day 13, and day 16 after the inoculation. On day 18 after the injection, the status of the tumor invasion was observed, the B16F10 tumors were surgically excised, and then the skin was sutured. In the untreated group, 50% of the tumor can be removed, and in the CMS5a ECV treatment group, 33% of the tumor can be removed. In all of the unremovable tumors, invasion to fascia was observed (see Table 1).

TABLE 1

Fascia Invasion of B16F10 after treatment with DUC18 ECVs, BALB/c ECVs, and CMS5aTB ECVs at the primary tumor sites.

| i.t. treatment | Number of mice with tumor invasion/total mice (%) |
| --- | --- |
| None | 6/12 (50%) |
| DUC18 ECVs | 0/13 (0%) |
| CMS5aTB ECVs | 2/3 (66.7%) |
| BALB/c ECVs | 0/3 (0%) |

B16F10-bearing mice exhibiting fascia invasion through tumor capsule (impossible to remove the primary tumors surgically) were counted.

Figure 16:
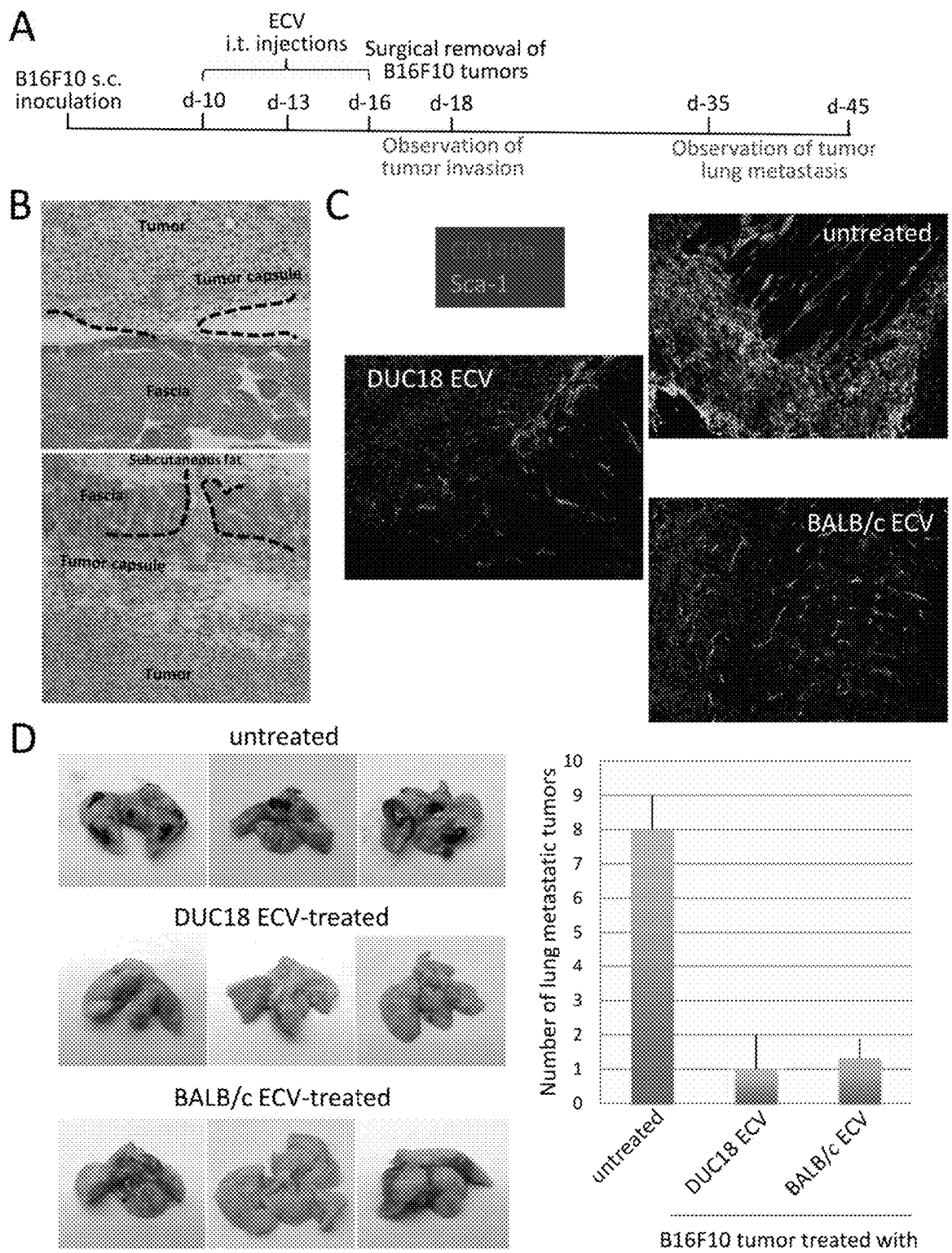
FIGS. 16A-16C concern the invasion and metastasis of B16F10 being suppressed by injecting DUC18 ECVs and BALB/c ECVs into primary tumors.
FIG. 16D shows photographs (left-side) of lung metastasis of the B16F10 tumors on day 45 after the tumor injection and a graph (right side) of the number of metastasized tumors that were found in each group (*<0.05, **<0.001).

On the other hand, in the DUC18 ECV- and BALB/c ECV-injected groups, all of the tumors were removable, and all mice survived on day 45 (FIG. 16A and FIG. 16B). In addition, on day 18 after the inoculation of the B16F10 cells, a decrease in CD140a$^+$ Sca-1$^+$ mesenchymal stroma was shown by immunohistological analysis in the mice that were intratumorally injected with DUC18 ECVs and BALB/c ECVs (FIG. 16C). As expected, lung metastasis of B16F10 was largely suppressed in the mice injected with DUC18 ECVs and BALB/c ECVs as compared to the untreated mice (FIG. 16D). These results demonstrate that ECVs released from CD8$^+$ T cells suppress aggravation of tumors.

Figure 17:
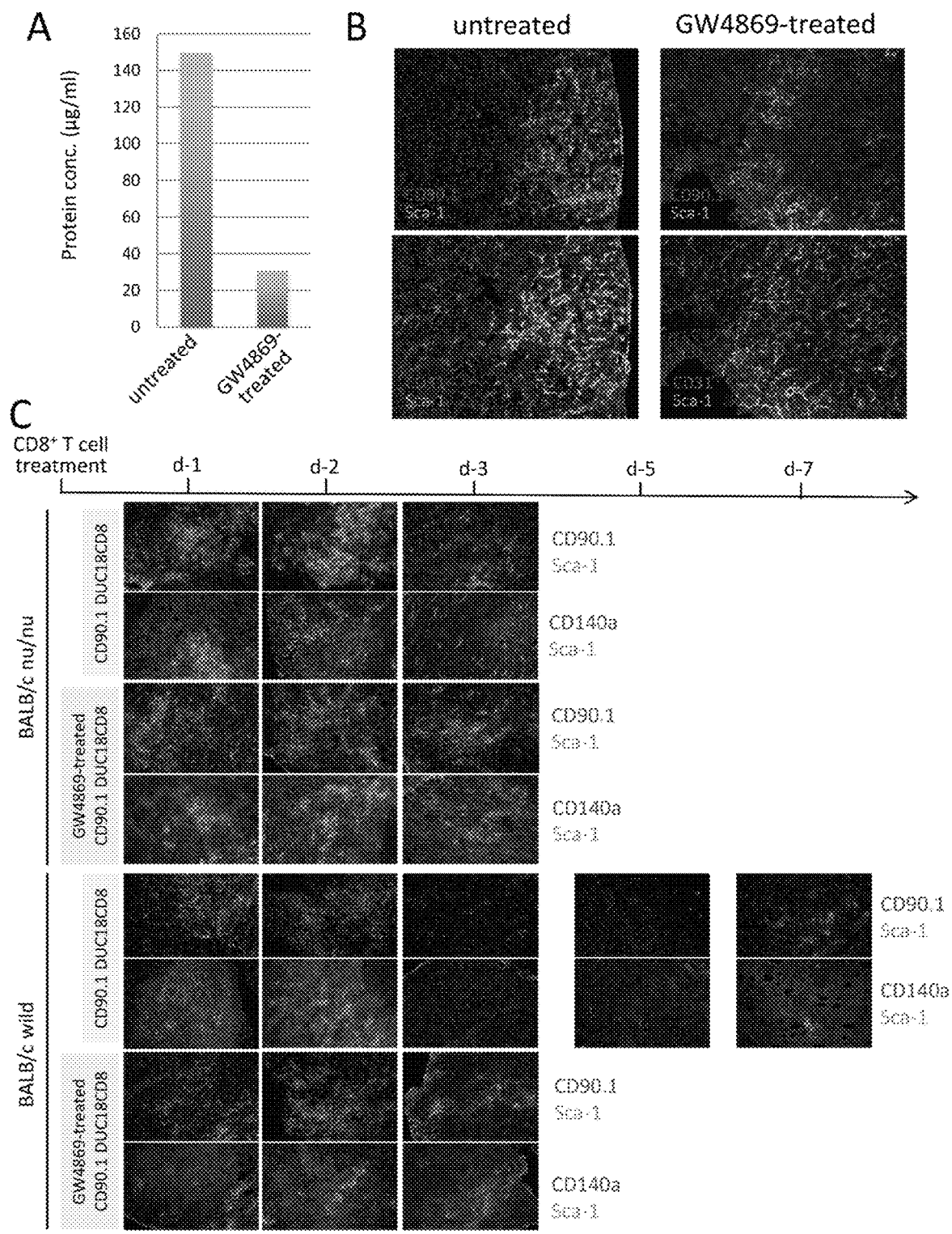
FIGS. 17A-17C concern the ability of CD8$^+$ T cells, which invaded from an angiogenic site of tumor lesion, to destroy tumor-associated stroma formation mediated by ECVs produced from these cells.
Figure 18:
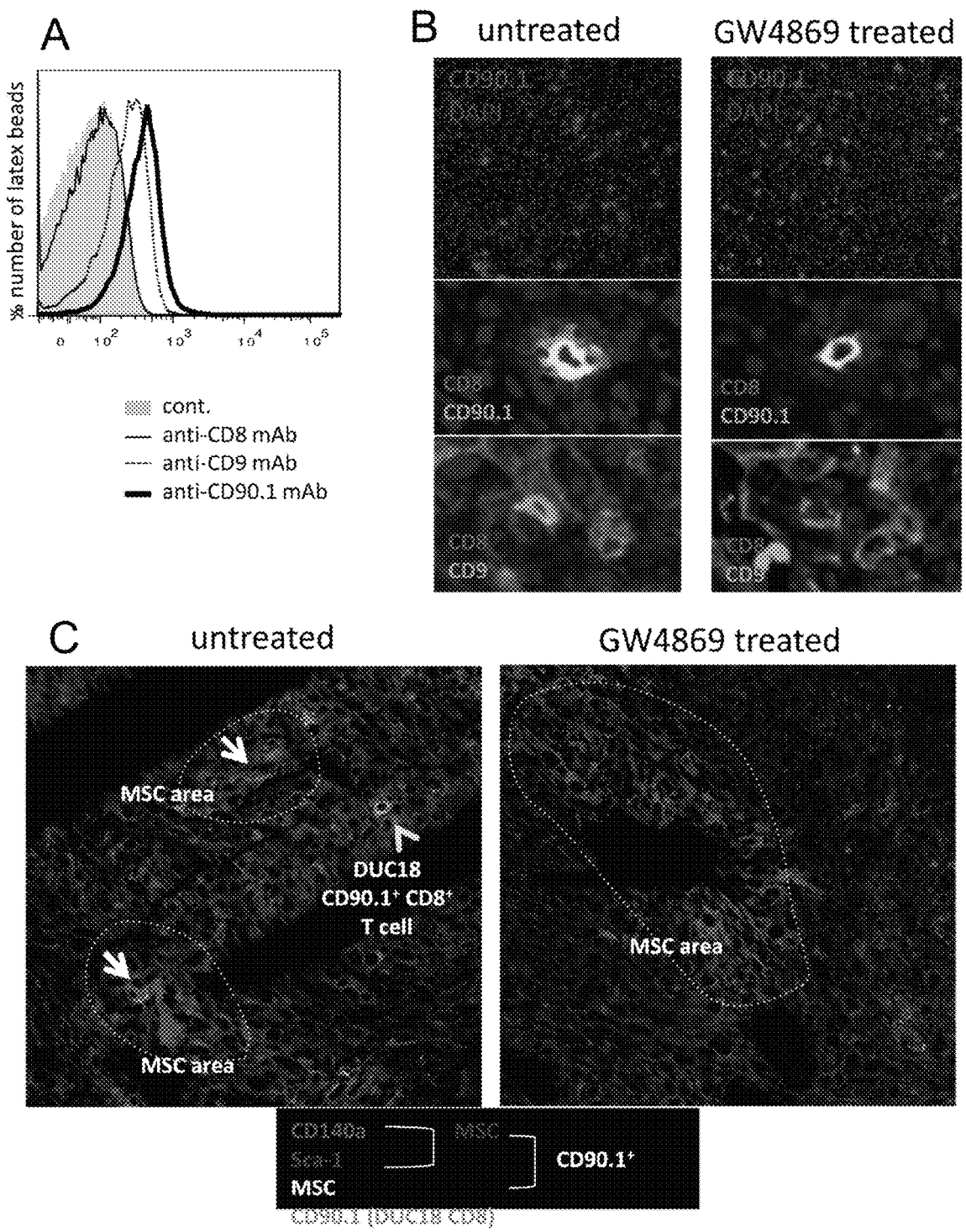
FIGS. 18A-18C also concern the ability of CD8+ T cells, which invaded from an angiogenic site of tumor lesion, to destroy tumor-associated stroma formation mediated by ECVs produced from these cells.

6. Peripheral Circulating Activated CD8$^+$ T Cells Intratumorally Invade at the Angiogenic Region, and Destroy Tumor-Associated Stromal Structure Finally, we investigated whether CD8$^+$ T cells would invade a tumor, and destroy tumor-associated stromal structure while releasing ECVs. BALB/c and BALB/c nude mice were subcutaneously inoculated with CMS5a. When the diameter of the CMS5a tumors became about 1 cm, the cultured CD90.1$^+$ DUC18 CD8$^+$ T cells, which were untreated or treated with GW4869 (an inhibitor of exosome production) (FIG. 17A), were intratumorally injected. The statuses of tumor-invaded-CD90.1$^+$ DUC18 CD8$^+$ T cells and stroma were investigated over time by immunostaining of tumor sections. Regardless of the GW4869 treatment or not, CD90.1$^+$ CD8$^+$ T cells were found in the Sca-1$^+$ CD31$^+$ angiogenic region of CMS5a tumor-associated stroma composed of endothelial precursor cells and BM-MSCs 24 hours after injection (FIG. 17B). Surprisingly, the Sca-1$^+$ or CD140a$^+$ region of the CMS5a tumor disappeared on day 3 after transfer of CD90.1$^+$ CD8$^+$ T cells, and this status persisted until day 7 (FIG. 17C). The effect of destroying stroma was found more in wild type BALB/c mice than in BALB/c nude mice. This may be due to intratumoral invasion of BALB/c-derived CD8$^+$ T cells together with injected CD90.1$^+$ CD8$^+$ T cells. Furthermore, since a disappearance of Sca-1$^+$ or CD140a$^+$ stroma was not observed in the group injected with GW4869-treated CD90.1$^+$ CD8$^+$ T cells (FIG. 17C), it was suggested that intratumorally invading CD8$^+$ T cells produce ECVs to destroy the tumor-associated stromal structure, similarly to the result where purified ECVs were used. CD90.1$^+$ ECVs released from CD8$^+$ T cells profusely express CD9 and CD90.1, and scarcely express CD8 (FIG. 18A). In the CMS5a tumors 24 hours after the injection of the CD90.1$^+$ CD8$^+$ T cells, ECV-derived CD9 and CD90.1 (FIG. 18B) and their fusion signal (FIG. 18C) were found in the CD140a$^+$ Sca-1$^+$ stromal region, but were not observed in the tumors of the GW4869-treated CD90.1$^+$ CD8$^+$ T cell-treated group.

Figure 19:
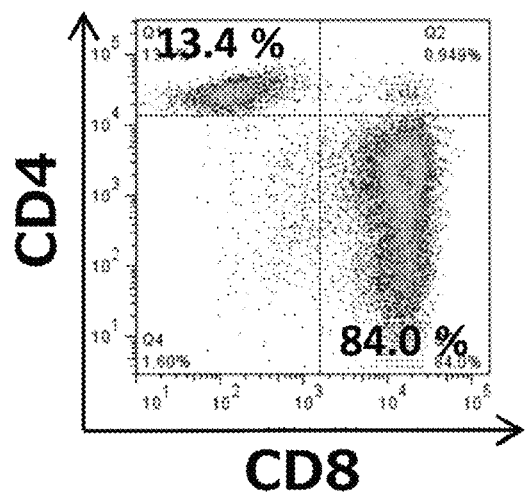
FIG. 19 graphically shows flow cytometry results of the CD4+ and CD8+ of the T cell population obtained from monocytes that were isolated from human peripheral blood and cultured for 2 weeks.
Figure 20:
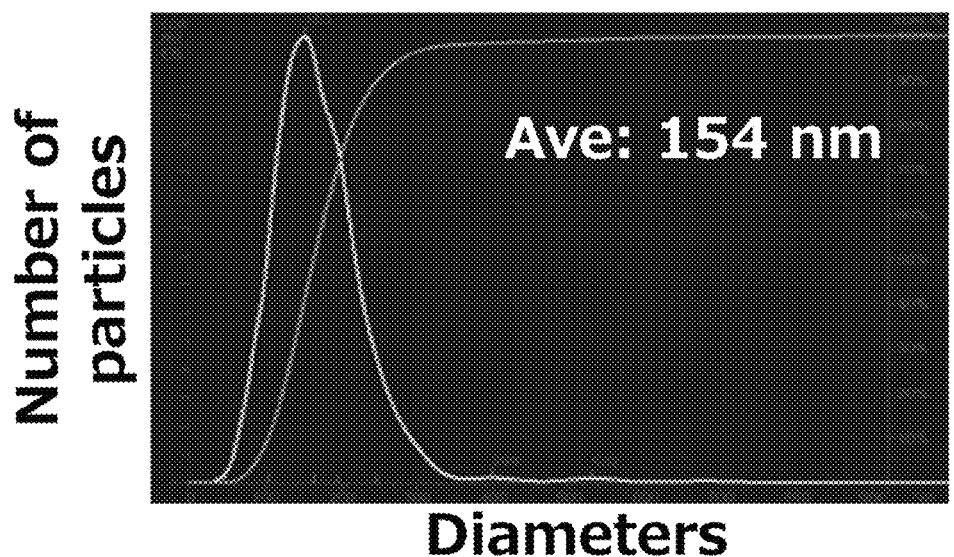
FIG. 20 is a graph illustrating the results of an investigation with respect the diameters of exosomes released from human T cells.

7. MSC Cytotoxic miRNA can be Identified in Exosomes Released from Cultured Human T Cells T cell populations obtained from monocytes separated from human peripheral blood were cultured for 2 weeks, and flow cytometry analysis demonstrated that the resulting T cell population was CD8 dominant (FIG. 19). Nano-Tracking Analysis demonstrated that the diameters of the exosomes released from these T cells into the culture supernatant were about 150 nm (FIG. 20).

Figure 21:
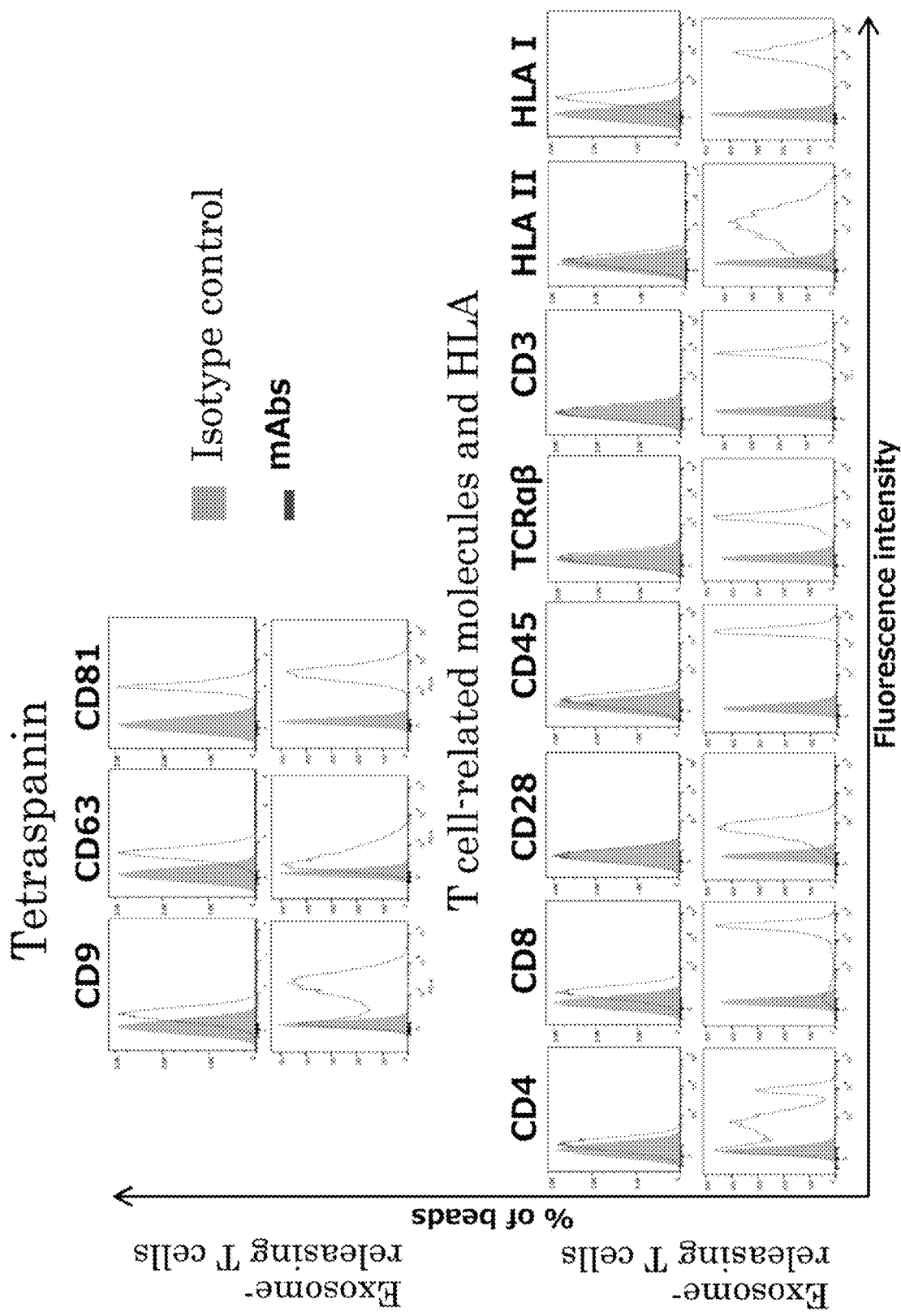
FIG. 21 contains graphs illustrating the results of flow cytometry analyses of surface molecules on exosomes released from human T cells and surface molecules on human T cells. The horizontal axes of these graphs indicate fluorescence intensities, and the vertical axes indicate percentages of the beads (%). The analyzed molecules are identified at the top of the respective graphs.

As a result of flow cytometry analysis of the surface antigens on the exosomes and cultured human T cells, tetraspanin molecules, which serve as exosome markers (CD9, CD63, CD81), CD8, and HLA class I molecules, were expressed (FIG. 21).

Figure 22:
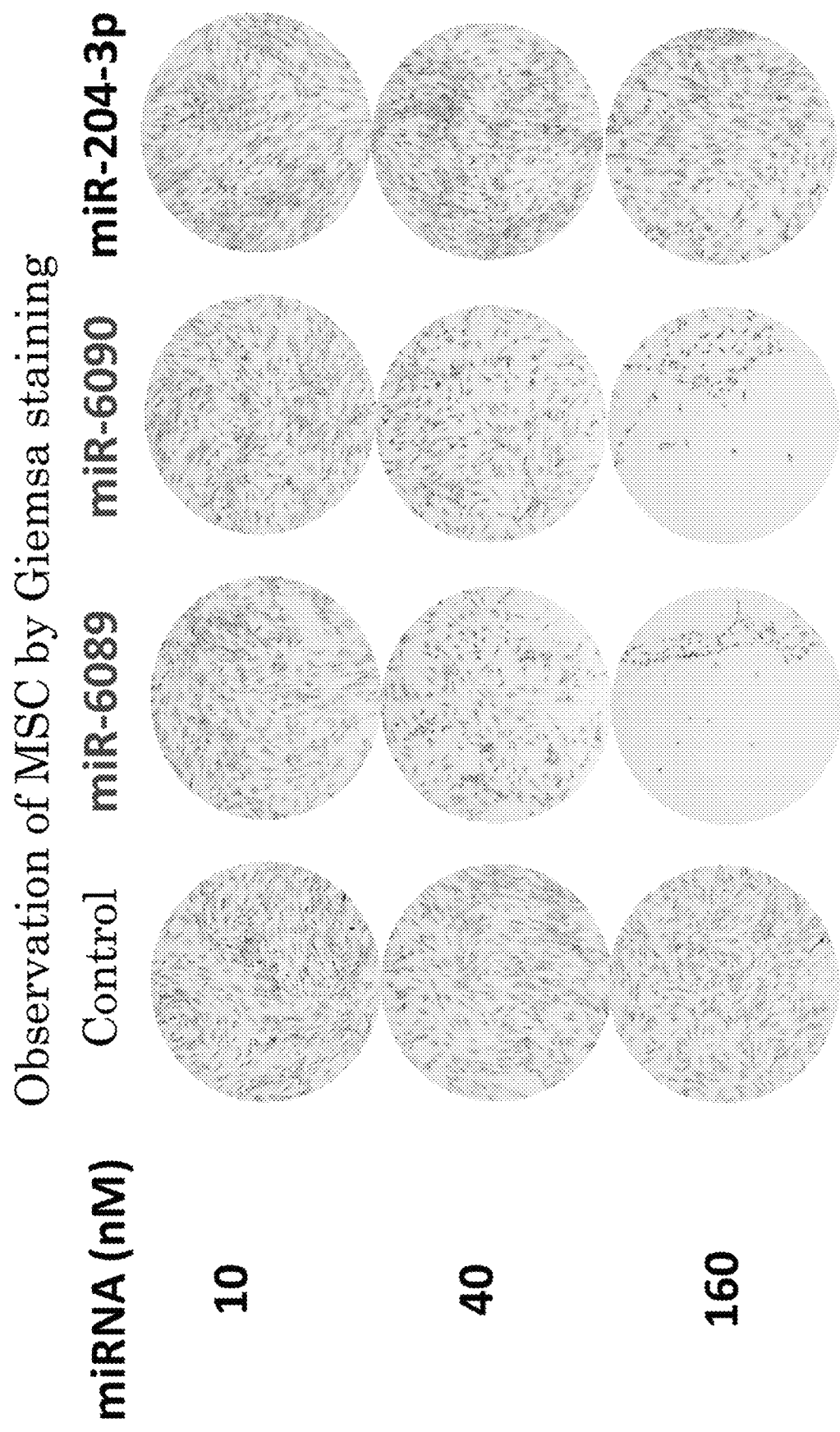
FIG. 22 contains twelve photographs that depict the results of investigating the effects of a variety of miRNA, which are contained in exosomes released from human T cells, on MSC. The various amounts of added miRNA are indicated in the vertical direction, and the types of added miRNA are indicated in the horizontal direction. miRNA was not added to the controls. Among 40 kinds of miRNAs, cytotoxicity to MSC was observed in the following two types: miR-6089 and miR-6090. miR-204-3p is illustrated as one not having cytotoxicity to MSC.
Figure 23:
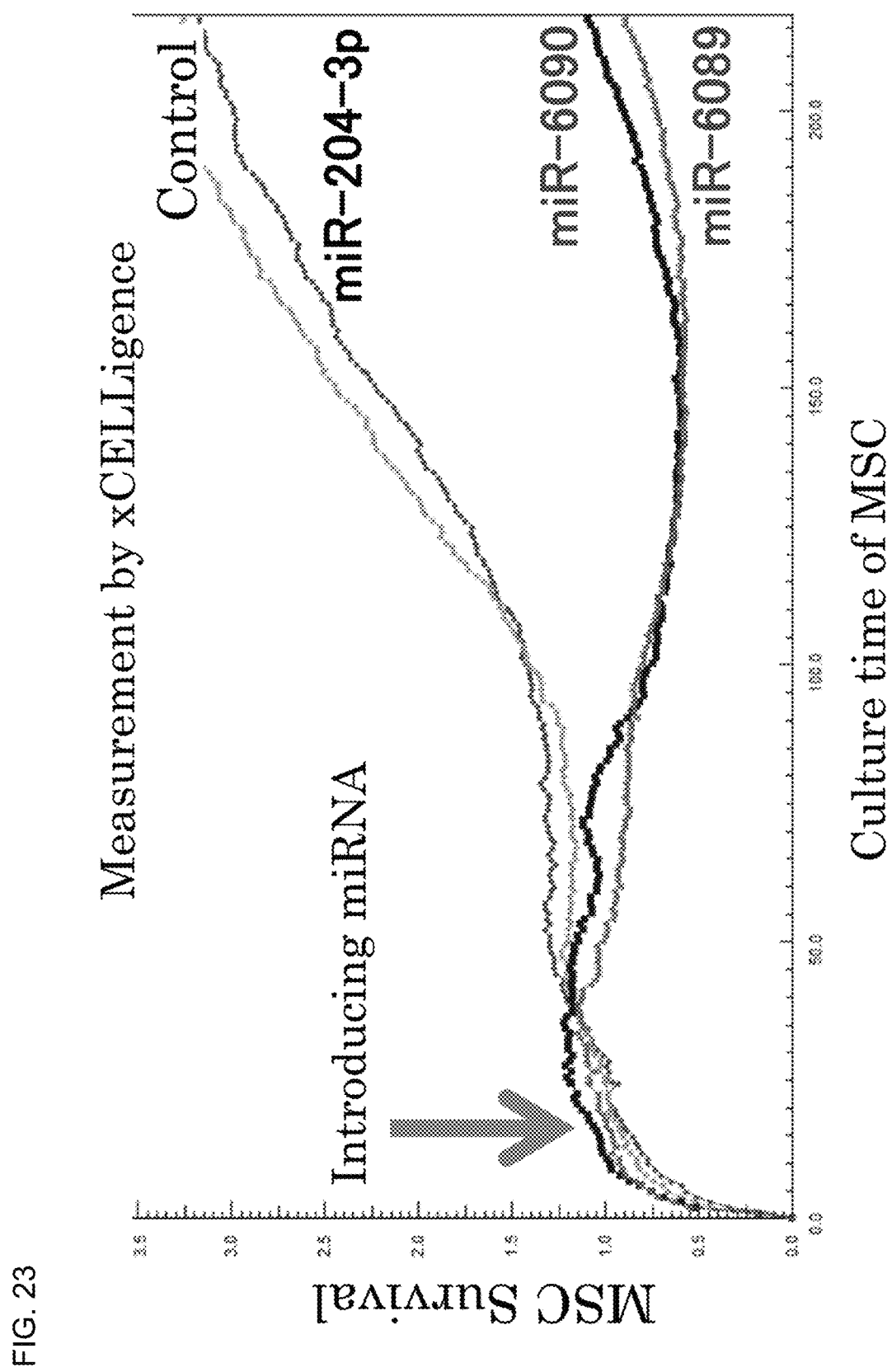
FIG. 23 a graph illustrating the results of investigating the effects of each miRNA on the survival of MSC. miRNA was added at the final concentration of 40 nM.

As a result of adding 40 types of miRNA contained in the exosomes to MSCs in culture and examining cytotoxic activity, 2 types of miRNA (miR-6089 and miR-6090) could be identified (FIG. 22 and FIG. 23).

The MSC cytotoxic miRNA thus obtained can be applied as a therapeutic agent for cell-proliferative disorders.

Since the immune system of humans is nearly similar to that of mice, the findings obtained in mice in vivo and in vitro can be directly applied to humans.

Thus, according to the present embodiment, a therapeutic agent associated with the suppression of proliferation and metastasis of tumors, which therapeutic agent includes exosomes released from cytotoxic T cells and targets cancer stromal/mesenchymal cells, can be provided.

Prior art literature related to the present teachings is listed below. It is noted that, although it was not explained in the specification with reference to their numbers, it is consistent with prior art of the present teachings.

Prior Art Literature

Non Patent Literature

Non Patent Literature 1: Houlihan D D, Mabuchi Y, Morikawa S, Niibe K, Araki D, Suzuki S, Okano H, Matsuzaki Y. Isolation of mouse mesenchymal stem cells on the basis of expression of Sca-1 and PDGFR-$\alpha$. Nat. Protoc. (2012) 7: 2103-2111.

Non Patent Literature 2: Vajkoczy P, Blum S, Lamparter M, Mailhammer R, Erber R, Engelhardt B, Vestweber D, Hatzopoulos A K. Multistep nature of microvascular recruitment of ex vivo-expanded embryonic endothelial progenitor cells during tumor angiogenesis. J. Exp. Med. (2003) 197: 1755-1765.

Non Patent Literature 3: Joyce J A, Pollard J W. Microenvironmental regulation of metastasis. Nat Rev Cancer. (2009) 9: 239-252.

Non Patent Literature 4: Tran E, Chinnasamy D, Yu Z, Morgan R A, Lee C C, Restifo N P, Rosenberg S A. Immune targeting of fibroblast activation protein triggers recognition of multipotent bone marrow stromal cells and cachexia. J Exp Med. (2013) 210: 1125-1135.

Non Patent Literature 5: Nieto M A. The ins and outs of the epithelial to mesenchymal transition in health and disease. Annu. Rev. Cell Dev. Biol. (2011) 27:347-376.

Non Patent Literature 6: Koh B I, Kang Y. The prometastatic role of bone marrow-derived cells: a focus on MSCs and regulatory T cells. EMBO reports. (2012) 13: 412-422.

Non Patent Literature 7: Nieto MA1, Cano A. The epithelial-mesenchymal transition under control: global programs to regulate epithelial plasticity. Semin. Cancer Biol. (2012) 22: 361-368.

Non Patent Literature 8: Filipazzia P, Burdeka M, Villab A, Rivoltinia L, Huber V. Recent advances on the role of tumor exosomes in immunosuppression and disease progression. Semin. Cancer Biol. (2012) 22: 342-349.

Non Patent Literature 9: Ono M, Kosaka N, Tominaga N, Yoshioka Y, Takeshita F, Takahashi R U, Yoshida M, Tsuda H, Tamura K, Ochiya T. Exosomes from bone marrow mesenchymal stem cells contain a microRNA that promotes dormancy in metastatic breast cancer cells. Sci Signal. (2014) 7: ra63.

Non Patent Literature 10: Boelens M C, Wu T J, Nabet B Y, Xu B, Qiu Y, Yoon T, Azzam D J, Twyman-Saint Victor C, Wiemann B Z, Ishwaran H, Ter Brugge P J, Jonkers J, Slingerland J, Minn A J. Exosome transfer from stromal to breast cancer cells regulates therapy resistance pathways. Cell. (2014) 159: 499-513.

Non Patent Literature 11: Webber J, Steadman R, Mason M D, Tabi Z, Clayton A. Cancer exosomes trigger fibroblast to myofibroblast differentiation. Cancer Res. (2010) 70: 9621-9630.

Non Patent Literature 12: Chalmin F, Ladoire S, Mignot G, Vincent J, Bruchard M, Remy-Martin J P, Boireau W, Rouleau A, Simon B, Lanneau D, De Thonel A, Multhoff G, Hamman A, Martin F, Chauffert B, Solary E, Zitvogel L, Garrido C, Ryffel B, Borg C, Apetoh L, Rebe C, Ghiringhelli F. Membrane-associated Hsp72 from tumor-derived exosomes mediates STAT3-dependent immunosuppressive function of mouse and human myeloid-derived suppressor cells. J. Clin. Invest. (2010) 120: 457-471.

Non Patent Literature 13: Pucci F, Pittet M J. Molecular pathways: tumor-derived microvesicles and their interactions with immune cells in vivo. Clin. Cancer Res. (2013) 19: 2598-2604.

Non Patent Literature 14: Roccaro A M, Sacco A, Maiso P, Azab A K, Tai Y T, Reagan M, Azab F, Flores L M, Campigotto F, Weller E, Anderson K C, Scadden D T, Ghobrial I M. B M mesenchymal stromal cell-derived exosomes facilitate multiple myeloma progression. J Clin Invest. (2013) 123: 1542-1555.

Non Patent Literature 15: Shimoda M, Principe S, Jackson H W, Luga V, Fang H, Molyneux S D, Shao Y W, Aiken A, Waterhouse P D, Karamboulas C, Hess F M, Ohtsuka T, Okada Y, Allies L, Ludwig A, Wrana J L, Kislinger T, Khokha R. Loss of the Timp gene family is sufficient for the acquisition of the CAF-like cell state. Nat. Cell Biol. (2014) 16: 889-901.

Non Patent Literature 16: Hinrichs CS1, Gattinoni L, Restifo N P. Programming CD8$^+$ T cells for effective immunotherapy. Curr. Opin. Immunol. (2006) 18: 363-370.

Non Patent Literature 17: Callahan M K, Wolchok J D. At the bedside: CTLA-4- and PD-1-blocking antibodies in cancer immunotherapy. J. Leukoc. Biol. (2013) 94: 41-53.

Non Patent Literature 18: Ishihara M, Seo N, Mitsui J, Muraoka D, Tanaka M, Mineno J, Ikeda H, Shiku H. Systemic CD8$^+$ T cell-mediated tumoricidal effects by intratumoral treatment of oncolytic herpes simplex virus with the agonistic monoclonal antibody for murine glucocorticoid-induced tumor necrosis factor receptor. PLoS One. (2014) 9: e104669.

Non Patent Literature 19: Prakash M D, Munoz M A, Jain R, Tong P L, Koskinen A, Regner M, Kleifeld O, Ho B, Olson M, Turner S J, Mrass P, Weninger W, Bird P I. Granzyme B promotes cytotoxic lymphocyte transmigration via basement membrane remodeling. Immunity. (2014) 41: 960-972.

Non Patent Literature 20: Ikeda, H., N. Ohta, K. Furukawa, H. Miyazaki, L. Wang, K. Kuribayashi, L. J. Old, and H. Shiku. 1997. Mutated mitogen-activated protein kinase: a tumor rejection antigen of mouse sarcoma. Proc. Natl. Acad. Sci. USA. 94:6375-6379.

Non Patent Literature 21: Ly L V, Sluijter M, van der Burg S H, Jager M J, van Hall T. Effective cooperation of monoclonal antibody and peptide vaccine for the treatment of mouse melanoma. J Immunol. (2013) 190: 489-496.

Non Patent Literature 22: Griffin MD1, Ritter T, Mahon B P. Immunological aspects of allogeneic mesenchymal stem cell therapies. Hum Gene Ther. 2010 December; 21(12): 1641-55.

Non Patent Literature 23: Bexell D, Gunnarsson S, Tormin A, Darabi A, Gisselsson D, Roybon L, Scheding S, Bengzon J. Bone marrow multipotent mesenchymal stroma cells act as pericyte-like migratory vehicles in experimental gliomas. Mol Ther. (2009) 17: 183-190.
Non Patent Literature 24: Eikawa S, Mizukami S, Udono H. Monitoring multifunctionality of immune-exhausted CD8 T cells in cancer patients. Methods Mol Biol. (2014) 1142: 11-17.
Non Patent Literature 25: Shimada M, Yoshizaki S, Ichino M, Klinman D M, Okuda K. Apoptosis of antigen-specific CTLs contributes to low immune response in gut-associated lymphoid tissue post vaccination. Vaccine. (2014) 32: 5198-5205.
Non Patent Literature 26: Arina A, Schreiber K, Binder D C, Karrison T G, Liu R B, Schreiber H. Adoptively transferred immune T cells eradicate established tumors despite cancer-induced immune suppression. J Immunol. (2014) 192: 1286-1293.
Non Patent Literature 27: Maciag P C, Seavey M M, Pan Z K, Ferrone S, Paterson Y. Cancer immunotherapy targeting the high molecular weight melanoma-associated antigen protein results in a broad antitumor response and reduction of pericytes in the tumor vasculature. Cancer Res. (2008) 68: 8066-8075.
Non Patent Literature 28: Ochs K, Sahm F, Opitz C A, Lanz T V, Oezen I, Couraud P O, von Deimling A, Wick W, Platten M. Immature mesenchymal stem cell-like pericytes as mediators of immunosuppression in human malignant glioma. J Neuroimmunol. (2013) 265: 106-116.
Non Patent Literature 29: Mi Z, Bhattacharya S D, Kim V M, Guo H, Talbot L J, Kuo P C. Osteopontin promotes CCL5-mesenchymal stromal cell-mediated breast cancer metastasis. Carcinogenesis. (2011) 32: 477-487.
Non Patent Literature 30: McDonald D M, Baluk P. Significance of Blood Vessel Leakiness in Cancer Cancer Res. (2002) 62: 5381-5385.
Non Patent Literature 31: Yoong K F, McNab G, Hubscher S G, Adams D H. Vascular adhesion protein-1 and ICAM-1 support the adhesion of tumor-infiltrating lymphocytes to tumor endothelium in human hepatocellular carcinoma. J Immunol. (1998) 160: 3978-3988.
Non Patent Literature 32: Nandi A1, Estess P, Siegelman M. Bimolecular complex between rolling and firm adhesion receptors required for cell arrest; CD44 association with VLA-4 in T cell extravasation. Immunity. (2004) 20: 455-465.
Non Patent Literature 33: Ding Z, Xiong K, Issekutz T B. Chemokines stimulate human T lymphocyte transendothelial migration to utilize VLA-4 in addition to LFA-1. J Leukoc Biol. (2001) 69: 458-466.
Non Patent Literature 34: Stauss H J, Morris E C. Immunotherapy with gene-modified T cells: limiting side effects provides new challenges. Gene Ther. (2013) 20: 1029-1032.
Non Patent Literature 35: Winograd R, Byrne K, Evans R A, Odorizzi P M, Meyer A R, Bajor D L, Clendenin C, Stanger B Z, Further E F, Wherry E J, Vonderheide R H. Induction of T cell immunity overcomes complete resistance to PD-1 and CTLA-4 blockade and improves survival in pancreatic carcinoma. Cancer Immunol Res. (2015) Feb. 12. pii: canimm.0215.2014.

The invention claimed is:

1. A method comprising:
subjecting cultured cytotoxic T cells to antigen stimulation,
collecting exosomes released from the cultured cytotoxic T cells 5-7 days after the antigen stimulation,
identifying miRNA from the collected exosomes that is effective in suppressing proliferation of mesenchymal cells surrounding cancer cells,
adding miRNA having a base sequence that is same as a base sequence of the miRNA, which was identified as being effective in suppressing proliferation of mesenchymal cells surrounding cancer cells, to cultured human mesenchymal stem cells (MSCs),
culturing the MSCs,
investigating toxic activity against the MSCs to evaluate MSC cytotoxicity of the miRNA, and
administering miRNA that was identified as being toxic to MSCs to a patient having cancer cells to kill mesenchymal cells surrounding the cancer cells and thereby suppress proliferation and/or metastasis of the cancer cells.

2. The method according to claim 1, wherein the cytotoxic T cells are CD8+ cells.

3. The method according to claim 1, wherein the step of investigating toxic activity against the MSCs is performed by counting a total number of remaining MSCs in the cultured MSCs by subjecting the remaining MSCs to flow cytometry.

4. The method according to claim 1, wherein the step of investigating toxic activity against the MSCs is performed by subjecting remaining MSCs to Giemsa staining or electrical resistance analysis.

5. The method according to claim 1, wherein the MSCs are bone marrow MSCs.

6. The method according to claim 1, wherein the step of collecting exosomes released from the cultured cytotoxic T cells is performed by ultracentrifuging culture supernatant from the cultured cytotoxic T cells to separate the exosomes from the cultured cytotoxic T cells.

7. The method according to claim 1, further comprising:
preparing by chemical synthesis the miRNA having a base sequence that is the same as a base sequence of the miRNA that is added to cultured human mesenchymal stem cells.

8. The method according to claim 2, wherein the MSCs are bone marrow MSCs.

9. The method according to claim 8, wherein the step of collecting exosomes released from the cultured cytotoxic T cells is performed by ultracentrifuging culture supernatant from the cultured cytotoxic T cells to separate the exosomes from the cultured cytotoxic T cells.

10. The method according to claim 9, further comprising:
preparing by chemical synthesis the miRNA having a base sequence that is the same as a base sequence of the miRNA that is added to cultured human mesenchymal stem cells.

11. The method according to claim 10, wherein the step of investigating toxic activity against the MSCs is performed by counting a total number of remaining MSCs in the cultured MSCs by subjecting the remaining MSCs to flow cytometry.

12. The method according to claim 10, wherein the step of investigating toxic activity against the MSCs is performed by subjecting remaining MSCs to Giemsa staining or electrical resistance analysis.

13. The method according to claim 10, further comprising administering miRNA that was identified as being toxic to MSCs to a patient having cancer cells to kill mesenchymal cells surrounding the cancer cells and thereby suppress proliferation and/or metastasis of the cancer cells.

\* \* \* \* \*